United States Patent [19]
Beard et al.

[11] Patent Number: 5,739,338
[45] Date of Patent: Apr. 14, 1998

[54] N-ARYL SUBSTITUTED TETRAHYDROQUINOLINES HAVING RETINOID AGONIST, RETINOID ANTAGONIST OR RETINOID INVERSE AGONIST TYPE BIOLOGICAL ACTIVITY

[75] Inventors: Richard L. Beard, Newport Beach; Min Teng, Aliso Viejo; Diana F. Colon; Tien T. Duong, both of Irvine; Roshantha A. Chandraratna, Mission Viejo, all of Calif.

[73] Assignee: Allergan, Irvine, Calif.

[21] Appl. No.: 744,210

[22] Filed: Nov. 5, 1996

[51] Int. Cl.$^6$ .................. C07D 215/227; A61K 31/47
[52] U.S. Cl. .................. 546/153; 546/165; 514/311; 514/312; 514/314
[58] Field of Search .................. 546/153, 165; 514/311, 312, 314

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 544/176 |
| 4,391,731 | 7/1983 | Boller et al. | 252/299.26 |
| 4,695,649 | 9/1987 | Magami et al. | 560/86 |
| 4,723,028 | 2/1988 | Shudo | 514/544 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |

(List continued on next page.)

FOREIGN PATENT DOCUMENTS

| | | |
|---|---|---|
| 0098591 | 1/1984 | European Pat. Off. . |
| 0130795 | 1/1985 | European Pat. Off. . |
| 170105A | 2/1986 | European Pat. Off. . |
| 0176032 | 4/1986 | European Pat. Off. . |
| 0176033 | 4/1986 | European Pat. Off. . |
| 0253302 | 1/1988 | European Pat. Off. . |
| 0272921 | 6/1988 | European Pat. Off. . |

(List continued on next page.)

OTHER PUBLICATIONS

A General Synthesis of Terminal and Internal Arylalkynes by the Palladium–Catalyzed Reaction of Alkynylzinc Reagents with Aryl Halides by Anthony O. King and Ei-ichi, J. Org. Chem., (1978) 43/2: pp. 358–360.

Conversion of Methyl Ketones into Terminal Acetylenes and (E)–Tri–substituted Olefins of Terpenoid Origin by Ei–ichi, et al., J. Org. Chem., (1980) 45/12: pp. 2526–2528.

(List continued on next page.)

Primary Examiner—C. Warren Ivy
Assistant Examiner—D. Margaret M. Mach
Attorney, Agent, or Firm—Gabor L. Szekeres; Robert J. Baran; Martin A. Voet

[57] ABSTRACT

Compounds of the formula

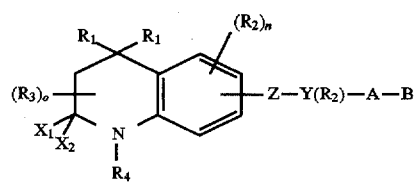

where the symbols have the meaning defined in the specification, have retinoid, retinoid antagonist or retinoid inverse agonist-like biological activity.

36 Claims, No Drawings

U.S. PATENT DOCUMENTS

| | | | |
|---|---|---|---|
| 5,514,825 | 5/1996 | Vuligonda et al. | 558/462 |
| 5,516,904 | 5/1996 | Chandraratna | 514/269 |
| 5,534,516 | 7/1996 | Chandraratna | 549/416 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,591,858 | 1/1997 | Vulogonda et al. | 546/322 |

FOREIGN PATENT DOCUMENTS

| | | |
|---|---|---|
| 0284261 | 8/1988 | European Pat. Off. . |
| 0284288 | 9/1988 | European Pat. Off. . |
| 0303915 | 2/1989 | European Pat. Off. . |
| 176034A | 4/1989 | European Pat. Off. . |
| 0315071 | 5/1989 | European Pat. Off. . |
| 0350846 | 7/1989 | European Pat. Off. . |
| 0661259 | 5/1995 | European Pat. Off. . |
| 3316932 | 11/1983 | Germany . |
| 3524199 | 1/1986 | Germany . |
| 3602473 | 7/1987 | Germany . |
| 3708060 | 9/1987 | Germany . |
| 3715955 | 11/1987 | Germany . |
| 2190378 | 11/1987 | United Kingdom . |
| 85/00806 | 2/1985 | WIPO . |
| 85/04652 | 10/1985 | WIPO . |
| 91/16051 | 10/1991 | WIPO . |
| 92/06948 | 4/1992 | WIPO . |
| 93/21146 | 10/1993 | WIPO . |

OTHER PUBLICATIONS

Sporn et al. in *J. Amer. Acad. Derm...*, (1986) 15:756–764.

"A Convenient Synthesis of Ethynylarenes and Diethynylarenes" by S. Takahashi et al. *Synthesis* (1980) pp. 627–630.

Shudo et al. in *Chem. Phar. Bull.*, (1985) 33:404–407.

Kagechika et al. in *J. Med. Chem.*, (1988) 31:2182–2192.

Chemistry and Biology of Synthetic Retinoids by Marcia I. Dawson and William H. Okamura, published by CRC Press Inc., 1990, pp. 334–335, 354.

Synthesis of 2,2'–Diacyl–1,1'–Biaryls. Regiocontrolled Protection of ... by Mervic, et al, *J. Org. Chem.*, (1980) No. 45, pp. 4720–4725.

A Dopamine Receptor Model and Its Application in the Design of a New Class of Rigid Pyrrolo[2,3–g]isoquinoline Antipsychotics, Gary L. Olson et al. *American Chemical Societe*, (1981) 24/9:1026–1031.

6.2.3 Conformational Restriction, Williams, et al., *Drug Discovery and Development*, The Humana Press, (1987) pp. 54–55.

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3, 341–438.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991), 34:2579–2588.

"Synthesis and Evaluatinof New Pretoein Tyrosine Kinase Inhibitors. Part 1. Pyridine–Containing Stilbenes and Amides" by Cushman, Mark et al. *Bioorganic & Medicinal Chemistry Letters*, (1991) 1/4:211–214.

"Di–and Tri–methoxystyryl Derivatives of Heterocyclic Nitrogen Compounds" by Bahner, C. T. et al. *Arzneim–Forsch./Drug Res.*, (1981)31 (I), Nr. 3, pp. 404–406.

"Retinobenzoic acids. 3. Structure–Activity Relationships of Retinoidal Azobenzene–4–Carboxylic Acids and Stilbene–4–Carboxylic Acids" by H. Kagechika et al., *Journal of Medicinal Chemistry*, (1989), 32:1098–1108.

Eyrolles, L. et al. "Retinoid Antagonists: Molecular Design Based on the Ligand Superfamily Concept" *Med. Chem. Res.*, (1992) 2:361–367.

Liu, S. S. et al. "Systemic Pharmacokinetics of Acetylenic Retinoids in Rats", *Drug Metabolism and Disposition*, (1990) 18/6: 1071–1077.

N-ARYL SUBSTITUTED TETRAHYDROQUINOLINES HAVING RETINOID AGONIST, RETINOID ANTAGONIST OR RETINOID INVERSE AGONIST TYPE BIOLOGICAL ACTIVITY

BACKGROUND OF THE INVENTION

1. Field of the Invention

The present invention relates to novel compounds having retinoid-like, retinoid antagonist and/or retinoid inverse-agonist-like biological activity. More specifically, the present invention relates to aryl substituted tetrahydroquinoline derivatives which bind to retinoid receptors and have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppresants and immunostimulants, modulation of organ transplant rejection and facilitation of wound healing, including modulation of chelosis.

U.S. Pat. No. 5,399,561 describes N-alkyl substituted tetrahydroquinoline-2-one derivatives which have retinoid-like biological activity. U.S. Pat. Nos. 4,980,369, 5,006,550, 5,015,658, 5,045,551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,407,937, (assigned to the same assignee as the present application) and patents and publications cited therein, deserve or relate to chroman, thiochroman and 1,2,3,4-tetrahydroquinoline derivatives which have retinoid-like biological activity. Still further, several co-pending applications and recently issued patents which are assigned to the assignee of the present application, are directed to further compounds having retinoid-like activity. Among these, pending application Ser. No. 08/442,223 describes N-phenyl alkyl (such as N-benzyl) substituted tetrahydroquinoline-2-one derivatives (and the corresponding thio analogs) which have retinoid-like biological activity.

Although pharmaceutical compositions containing retinoids have well established utility (as is demonstrated by the foregoing citation of patents and publications from the voluminous literature devoted to this subject) retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXB_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist), the compound may elicit an agonist-like response on all receptor subtypes (pan-agonist), or a compound may be a partial agonist and/or partial antagonist of certain receptor subtypes if the compound binds to but does not activate certain receptor subtype or subtypes but elicits an agonist-like response in other receptor subtype or subtypes. A pan antagonist is a compound that binds to all known retinoid receptors but does not elicit an agonist-like response in any of the receptors.

Recently a two-state model for certain receptors, including the above-mentioned retinoid receptors, have emerged.

In this model, an equilibrium is postulated to exist between inactive receptors and spontaneously active receptors in the absence of a ligand. In this model, so-called "inverse agonists" shift the equilibrium toward inactive receptors, thus bringing about an overall inhibitory effect of the basal level of activity. Neutral antagonists do not effect the receptor equilibrium but are capable of competing for the receptors with both agonists and inverse agonists.

It has been recently discovered and described in a pending application assigned to the same assignee as the present application that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well. More particularly, regarding the published scientific and patent literature in this field, published PCT application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. J Med. Chem. 1995, 38, 3163–3173. Kaneko et al. Med. Chem Res. (1991) 1:220–225; Apfel et al. Proc. Natl. Acad. Sci. USA Vol 89 pp 7129–7133 Augusty 1992 Cell Biology; Eckhardt et al. Toxicology Letters, 70 (1994) 299–308; Keidel et al. Molecular and Cellular Biology, Vol 14, No. 1, January 1994, p 287–298; and Eyrolles et al. J. Med. Chem. 1994, 37, 1508–1517 describe compounds which have antagonist like activity at one or more of the RAR retinoid subtypes.

SUMMARY OF THE INVENTION

The present invention relates to compounds of Formula 1

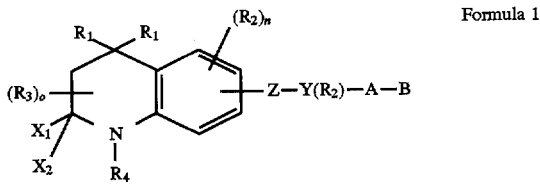

Formula 1 where $R_1$ is independently H or alkyl of 1 to 6 carbons;

$R_2$ is lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

n is an integer between the values 0 and 3;

$R_3$ is hydrogen, lower alkyl of 1 to 6 carbons or F;

o is an integer between the values 0–2;

$X_1$ and $X_2$ independently are H, or alkyl of 1 to 6 carbons, or F, or the $X_1$ and $X_2$ groups jointly symbolize an oxo (=O) or thio (=S) function;

$R_4$ is phenyl, naphthyl or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being optionally substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, or $COOR_1$;

Z is —C≡C—

—N=N—,

—N(O)=N—,

—N=N(O)—,

—N=CR_1—,

—CR_1=N,

—(CR_1=CR_1)_{n'}— where n' is an integer having the value 0–5,

—CO—NR_1—,

—CS—NR_1—,

—NR_1—CO,

—NR_1—CS,

—COO—,

—OCO—;

—CO—CR_1=CR_1—

—CSO—;

—OCS—;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —(CR_1=CR_1)_{n'}— and n' is 3, 4 or 5 then Y represents a direct valence bond between said $(CR_2=CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, pre-malignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreo-retinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment Or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assay of Retinoid-like or Retinoid Antagonist and Inverse Agonist-like Biological Activity.

A classic measure of retinoic acid activity involves measuring the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. Activity of exemplary compounds of the present invention in the above-described ODC assay is disclosed in Table 1 which provides the IC$_{60}$ concentration for the respective exemplary compound. ("IC$_{60}$" is that concentration of the test compound which causes 60% inhibition in the ODC assay. By analogy, "IC$_{80}$", for example, is that concentration of the test compound which causes 80% inhibition in the ODC assay.)

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a K$_d$ value of less than approximately 1 micromolar. In the below descried assays the ability of the compounds to bind to RAR$_\alpha$, RAR$_\beta$, RAR$_\gamma$, RXR$_\alpha$, RXR$_\beta$ and RXR$_\Gamma$ receptors, and the ability or inability of the compounds to activate transcription of a reporter gene through these receptor subtypes can be tested.

Specifically, a chimeric receptor transactivation assay which tests for agonist-like activity in the RAR$_\alpha$, RAR$_\beta$, RAR$_\gamma$, RXR$_\alpha$ receptor subtypes, and which is based on work published by Feigner P. L. and Holm M. (1989) Focus, 11 2 is described in detail in U.S. Pat. No. 5,455,265 the specification of which is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the holoreceptor transactivation assay is also provided below.

HOLORECEPTOR TRANSACTIVATION ASSAY

CV1 cells (5,000 cells/well) were transfected with an RAR reporter plasmid MTV-TREp-LUC (50 ng) along with one of the RAR expression vectors (10 ng) in an automated 96-well format by the calcium phosphate procedure of Heyman et al. Cell 68, 397–406, (1992). For RXR$_\alpha$ and RXR$_\gamma$ transactivation assays, an RXR-responsive reporter plasmid CRBPII-tk-LUC (50 ng) along with the appropriate RXR expression vectors (10 ng) was used substantially as described by Heyman et al. above, and Allegretto et al. J. Biol. Chem. 268, 26625–26633. For RXR$_\beta$ transactivation assays, an RXR-responsive reporter plasmid CPRE-tk-LUC (50 mg) along with RXR$_\beta$ expression vector (10 mg) was used as described in above. These reporters contain DRI elements from human CRBPII and certain DRI elements from promoter, respectively. (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. The results obtained in this assay are expressed in EC$_{50}$ numbers, as they are also in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York, are expressly incorporated herein by reference. The results of ligand binding assay are expressed in $K_d$ numbers. (See Cheng et al. Biochemical Pharmacology Vol. 22 pp 3099–3108, expressly incorporated herein by reference.)

Table 1 shows the results of the ligand binding assay for certain exemplary compounds of the invention for the receptor subtypes in the RAR group.

TABLE 1

| Compound No. | Ligand Binding Assay $K_d$ (nanomolar, nM) | | |
|---|---|---|---|
| | RARα | RARβ | RARγ |
| 5 | 13 | 3 | 9 |
| 10 | 147 | 18 | 52 |
| 12 | 101 | 84 | 530 |
| 14 | 11 | 5 | 15 |
| 22 | 59 | 17 | 32 |
| 25 | 27 | >$10^3$ | >$10^3$ |

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference.

In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. EMBO J. 12, 2349–2360 (1933) expressly incorporated herein by reference. Retinoid inverse agonists are able to inhibit the basal luciferase activity in these cells in a dose dependent manner and $IC_{50}$s measured. In this assay, Compound 5 had an $IC_{50}$ of 1 nM.

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic ache or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, ache, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/ or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per milliliter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. Still further oxime and related compounds of the present invention may exist in syn and anti isomeric forms. The scope of the present invention is intended to cover all such isomers per se, as well as mixtures of cis and trans isomers, mixtures of syn and anti isomers, mixtures of diastereomers and racemic mixtures of enantiomers (optical isomers) as well. In the present application when no specific mention is made of the configuration (cis, trans, syn or anti or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended.

Generally speaking, the compounds of the invention are prepared in synthetic steps which usually first involve the preparation of a tetrahydroquinoline intermediate that is appropriately substituted with the $R_1$, $R_2$, $R_3$, $R_4$, $X_1$ and $X_2$ substituents (defined in connection with Formula 1) and also with a reactive group, such as a Br or OH group, attached to the aromatic portion of the tetrahydroquinoline nucleus. The reactive group is thereafter converted to a another reactive function, such as $NH_2$, SH, or COOH which is then coupled to a reagent that together with the $NH_2$, SH, or COOH completes the moiety designated Z in Formula 1, and which also introduces the $Y(R_2)$—A—B moiety of the compounds of the invention. Compounds of the invention where Z represents an ester, amide, thioester, thioamide, or azo linkage can, for example, be prepared in accordance with this general synthetic methodology.

The reactive group (such as Br) attached to the aromatic portion of the tetrahydroquinoline nucleus can also be reacted with (trimethylsilyl)acetylene to provide a (trimethylsilyl)ethynyl-substituted N-aryl tetrahydroquinoline. The latter is coupled with a reagent of the formula $X_3$—$Y(R_2)$—A—B where $X_3$ is a halogen and the remaining symbols are defined in connection with Formula 1. Compounds of the invention where Z represents an ethynyl group are, generally speaking, prepared in this manner.

To obtain still other compounds of the invention, a coupling reaction is performed with the bromo substituted tetrahydroquinoline compound to provide products where the Y group is directly coupled to the tetrahydroquinoline nucleus. Alternatively a Heck coupling reaction provides compounds of the invention where the Y group is attached to the tetrahydroquinoline nucleus with an an ethenyl (or substituted ethenyl) function.

Still further, the Z—$Y(R_2)$—A—B moiety can be formed in multiple steps starting with the introduction of a two-carbon moiety (such as the $CH_3CO$ group) in place of the reactive bromo group of the N-aryl tetrahydroquinoline nucleus. This type of reaction sequence is suitable, for example, for the preparation of compounds of the invention where Z is —$(CR_1=CR_1)n$,—, n' is 3, 4 or 5 and Y represents a direct valence bond between the $(CR_2=CR_2)_n$. group and B. Details of the above-outlined generalized synthetic schemes are provided below in connection with the description of the specific embodiments and specific examples.

The synthetic methodology employed for the synthesis of the compounds of the present invention may also include transformations of the group designated —A—B in Formula 1. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodfimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of q in the compounds of the invention (or precursors thereof) before affecting the coupling or linkage with the tetrahydroquinoline nucleus (where such compounds are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of the invention as set forth in Formula 1 (or precursors thereof) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of the invention or precursors thereof, where the A group has a triple (acetylenic) bond, can be made by reaction of a corresponding aromatic methyl ketone with strong base, such as lithium diisopropylamide, reaction with diethyl chlorophosphate and subsequent addition of lithium diisopropylamide.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means. Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tel. Lett., 399, 1979), or dimethyl sulfoxide/oxalyl chloride in methylene chloride (Oreurn, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of the invention, or precursors thereof, where B is H can be prepared from .the corresponding halogenated aromatic or heteroaromatic compounds, preferably where the halogen is I.

SPECIFIC EMBODIMENTS

With reference to the symbol Y in Formula 1, the preferred compounds of the invention are those where Y is phenyl, naphthyl, pyridyl, thienyl or furyl. Even more preferred are compounds where Y is phenyl. As far as substitutions on the Y (phenyl), Y (pyridyl) and (Y) naphthyl groups are concerned, compounds are preferred where the phenyl group is 1,4 (para) substituted, the naphthyl group is 2,6 substituted and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no or only one optional $R_2$ substituent on the Y group, and the preferred $R_2$ substituent is fluoro (F).

The A—B group of the preferred compounds is $(CH_2)_q$COOH or $(CH_2)_1$—(COOR$_8$, where $R_8$ is defined as above. Even more preferably q is zero and $R_8$ is lower alkyl.

The aromatic portion of the tetrahydroquinoline moiety is preferably substituted only by the —Z—Y(R$_2$)—A—B group. In other words, in the preferred compounds there is no $R_2$ substituent (other than hydrogen) on the tetrahydroquinoline nucleus. Similarly, in the preferred compounds of the invention there is no $R_3$ substituent (other than hydrogen). The $R_1$ substituent of the compounds of the invention is preferably lower alkyl, and even more preferably methyl. The —Z—Y(R$_2$)—A—B group is preferably attached to the tetrahydroquinoline nucleus in its 6 or 7 position, more preferably in the 7 position. The numbering of the tetrahydroquinoline nucleus used in this application is in accordance with IUPAC rules, and is illustrated in connection with Formula 1A.

$X_1$ and $X_2$ are preferably, H, lower alkyl, or the two symbols jointly represent an oxo (=O) group. Even more preferably $X_1$ and $X_2$ are both H, or jointly represent an oxo (=O) group.

Preferred Z groups are:

—C≡C—, —CH=CH—, —CONH—, —COO—, —COS—, —CSNH—, —OCO—, —SCO, —NHCO—, —NHCS— —(CR$_1$=CR$_1$)n,— and n' is 3, or the Z group is absent (Y is directly attached to the tetrahydroquinoline nucleus). Among the foregoing even more preferred are the following: —C≡C—,—C=C—, and —CONH—.

The presently preferred $R_4$ groups are phenyl, alkyl or halogen substituted phenyl, furyl, alkyl or halogen substituted furyl, thienyl, alkyl or halogen substituted thienyl, pyridyl, and alkyl or halogen substituted pyridyl. Even more preferred are compounds where the $R_4$ group is phenyl or alkyl substituted phenyl, particularly (4-methyl)phenyl.

The most preferred compounds in accordance with Formula 1 are listed below in Table 2 for Formula 1A and with reference to that formula.

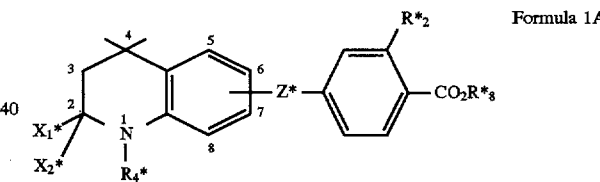

Formula 1A

TABLE 2

| Compound # | X*$_1$ | X*$_2$ | R*$_4$ | Z* | R$_2$* | R$_8$* |
|---|---|---|---|---|---|---|
| 4 | H | H | (4-methyl)phenyl | —C≡C— | H | Et |
| 5 | H | H | (4-methyl)phenyl | —C≡C— | H | H |
| 9 | H | H | phenyl | —C≡C— | H | Et |
| 10 | H | H | phenyl | —C≡C— | H | H |
| 11 | H | H | (4-methyl)phenyl | —C≡C— | F | Et |
| 12 | H | H | (4-methyl)phenyl | —C≡C— | F | H |
| 13 | H | H | (4-methyl)phenyl | —CH=CH— | H | Et |
| 14 | H | H | (4-methyl)phenyl | —CH=CH— | H | H |
| 21 | O$^1$ | — | (4-methyl)phenyl | —C≡C— | H | Et |
| 22 | O$^1$ | — | (4-methyl)phenyl | —C≡C— | H | H |
| 24 | H | H | (4-methyl)phenyl | —CO—NH— | H | Et |
| 25 | H | H | (4-methyl)phenyl | —CO—NH— | H | H |

$^1$The X$_1$* and X$_2$* symbols jointly represent an oxo group.

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will

Reaction Scheme 1

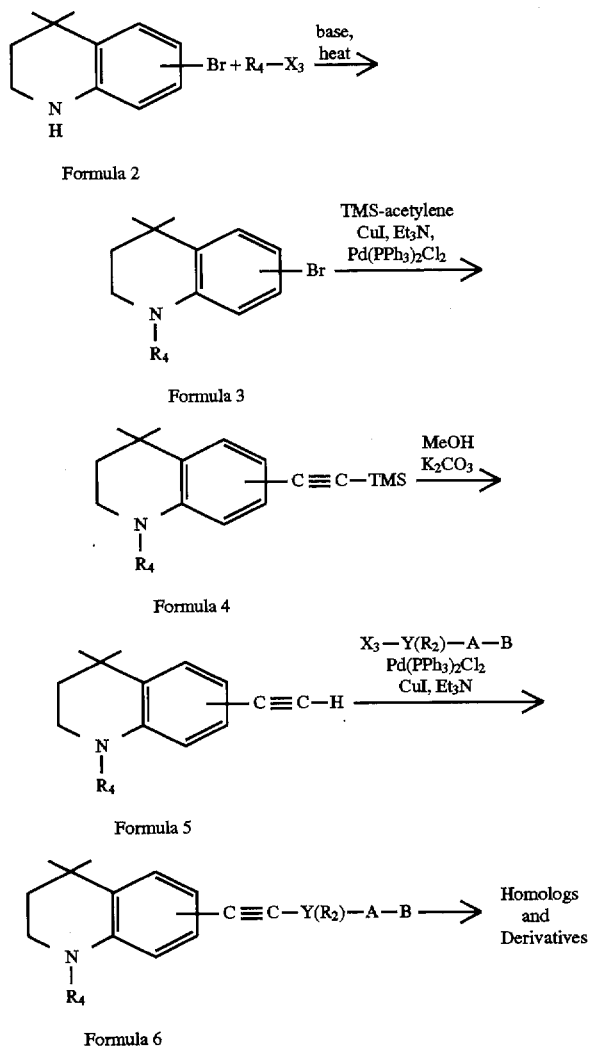

Formula 2

Formula 3

Formula 4

Formula 5

Formula 6

Referring now to Reaction Scheme 1 a synthetic process is described whereby compounds of the invention are obtained in which, with reference to Formula 1, the Z group is ethynyl (—C≡C—) and the $X_1$ and $X_2$ groups are both hydrogen. The starting compounds for this synthesis are 4,4-dimethyl-6-bromo-1,2,3,4-tetrahydroquinoline and 4,4-dimethyl-7-bromo-1,2,3,4-tetrahydroquinoline. For preparation of the 6-bromo isomer see U.S. Pat. No. 5,348,972 (Column 26), the specification of which is expressly incorporated herein by reference. Preparation of the 7-bromo positional isomer is described in the experimental section below, in three synthetic steps starting from commercially available 3-bromoaniline. It should be understood that although Reaction Scheme 1 describes a synthetic route where with reference to Formula 1 there is no $R_2$, $R_3$ substituent and $R_1$ is methyl, a similar reaction sequence can be carried out with 1,2,3,4-tetrahydrobromoquinoline derivatives which are substituted within the scope of Formula 1. In accordance with Reaction Scheme 1 the 1,2,3,4-tetrahydrobromoquinoline derivative is reacted with a reagent of the formula $R_4$—$X_3$, where $R_4$ is defined as above in connection with Formula 1 and $X_3$ is a leaving group, preferably halogen, for example iodine. Presently preferred examples for the reagent $R_4$—$X_3$ are 4-iodotoluene and iodobenzene. Other examples are 4-ethyliodobenzene, 3,5-dimethyliodobenzene, 4-fluoroiodobenzene, 4-nitroiodobenzene, ethyl-4-iodobenzoate, iodopyridine, iodofurane, and iodothiophene. The reaction between compounds of Formula 2 and $R_4$—$X_3$ is preferably conducted at high temperature, in the presence of a base and copper(I) iodide catalyst. The products of this reaction are N-aryl tetrahydroquinoline derivatives of Formula 3. In the next step, compounds of Formula 3 are reacted with (trimethylsilyl)acetylene in the presence of copper(I)iodide, triethylamine and bis(triphenylphosphine)palladium(II) chloride to yield N-aryl 6 or 7-(trimethylsilyl) ethynylquinoline derivatives of Formula 4. The trimethylsilyl group is removed from the latter by treatment with base, such as potassium carbonate, in alcoholic solvent (eg. methanol), to yield N-aryl 6 or 7-(ethynyl)quinoline derivatives of Formula 5. The N-aryl 6 or 7-(ethynyl)quinoline derivatives of Formula 5 are then coupled with the reagent of the formula $X_3$—Y($R_2$)—A—B (where $X_3$ is a halogen and the remaining symbols are defined in connection with Formula 1) in the presence of copper(I)iodide, triethylamine and bis(triphenylphosphine)palladium(II) chloride to provide compounds of Formula 6 which are within the scope of the present invention. Examples for the reagent $X_3$—Y($R_2$)—A—B are ethyl 4-iodobenzoate, ethyl 6-bromo-2-naphthoate, ethyl 6-iodonicotinate, ethyl 2-iodofuran-5-carboxylate, and ethyl 2-iodothiophen-5-carboxylate. Precise conditions of the reactions leading from compounds of Formula 3 to the compounds of Formula 6 are described in connection with the specific examples. These reactions are analogous to the reaction described in several United States Letters Patent, such as U.S. Pat. Nos. 5,348,972 and 5,346,915, assigned to the assignee of the present application, where introduction of an ethynyl group into a heteroaryl nucleus and subsequent coupling with a halogenated aryl or heteroaryl function are described. The specifications of U.S. Pat. Nos. 5,348,972 and 5,346,915 are specifically incorporated herein by reference. The compounds of Formula 6 can be converted into further homologs and derivatives in reactions of the type generally described above. A frequently used reaction in this regard is saponification whereby an ester function (represented in Formula 6 by the symbol B) is converted into a carboxylic acid function.

Reaction Scheme 2

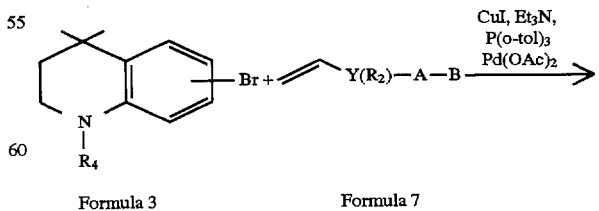

Formula 3        Formula 7

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means. Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tel. Lett., 399, 1979), or dimethyl sulfoxide/oxalyl chloride in methylene chloride (Oreurn, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of the invention, or precursors thereof, where B is H can be prepared from .the corresponding halogenated aromatic or heteroaromatic compounds, preferably where the halogen is I.

SPECIFIC EMBODIMENTS

With reference to the symbol Y in Formula 1, the preferred compounds of the invention are those where Y is phenyl, naphthyl, pyridyl, thienyl or furyl. Even more preferred are compounds where Y is phenyl. As far as substitutions on the Y (phenyl), Y (pyridyl) and (Y) naphthyl groups are concerned, compounds are preferred where the phenyl group is 1,4 (para) substituted, the naphthyl group is 2,6 substituted and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no or only one optional $R_2$ substituent on the Y group, and the preferred $R_2$ substituent is fluoro (F).

The A—B group of the preferred compounds is $(CH_2)_q$COOH or $(CH_2)_1$—$(COOR_8)$, where $R_8$ is defined as above. Even more preferably q is zero and $R_8$ is lower alkyl.

The aromatic portion of the tetrahydroquinoline moiety is preferably substituted only by the —Z—Y($R_2$)—A—B group. In other words, in the preferred compounds there is no $R_2$ substituent (other than hydrogen) on the tetrahydroquinoline nucleus. Similarly, in the preferred compounds of the invention there is no $R_3$ substituent (other than hydrogen). The $R_1$ substituent of the compounds of the invention is preferably lower alkyl, and even more preferably methyl. The —Z—Y($R_2$)—A—B group is preferably attached to the tetrahydroquinoline nucleus in its 6 or 7 position, more preferably in the 7 position. The numbering of the tetrahydroquinoline nucleus used in this application is in accordance with IUPAC rules, and is illustrated in connection with Formula 1A.

$X_1$ and $X_2$ are preferably, H, lower alkyl, or the two symbols jointly represent an oxo (=O) group. Even more preferably $X_1$ and $X_2$ are both H, or jointly represent an oxo (=O) group.

Preferred Z groups are:
—C≡C—, —CH=CH—, —CONH—, —COO—, —COS—, —CSNH—, —OCO—, —SCO, —NHCO—, —NHCS— —($CR_1$=$CR_1$)n,— and n' is 3, or the Z group is absent (Y is directly attached to the tetrahydroquinoline nucleus). Among the foregoing even more preferred are the following: —C≡C—, —C=C—, and —CONH—.

The presently preferred $R_4$ groups are phenyl, alkyl or halogen substituted phenyl, furyl, alkyl or halogen substituted furyl, thienyl, alkyl or halogen substituted thienyl, pyridyl, and alkyl or halogen substituted pyridyl. Even more preferred are compounds where the $R_4$ group is phenyl or alkyl substituted phenyl, particularly (4-methyl)phenyl.

The most preferred compounds in accordance with Formula 1 are listed below in Table 2 for Formula 1A and with reference to that formula.

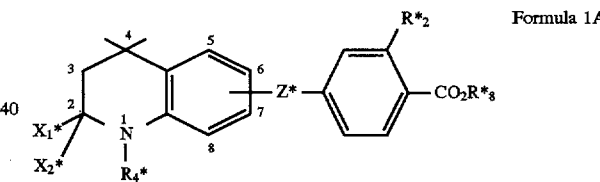

Formula 1A

TABLE 2

| Compound # | $X^*_1$ | $X^*_2$ | $R^*_4$ | $Z^*$ | $R_2^*$ | $R_8^*$ |
|---|---|---|---|---|---|---|
| 4 | H | H | (4-methyl)phenyl | —C≡C— | H | Et |
| 5 | H | H | (4-methyl)phenyl | —C≡C— | H | H |
| 9 | H | H | phenyl | —C≡C— | H | Et |
| 10 | H | H | phenyl | —C≡C— | H | H |
| 11 | H | H | (4-methyl)phenyl | —C≡C— | F | Et |
| 12 | H | H | (4-methyl)phenyl | —C≡C— | F | H |
| 13 | H | H | (4-methyl)phenyl | —CH=CH— | H | Et |
| 14 | H | H | (4-methyl)phenyl | —CH=CH— | H | H |
| 21 | O¹ | — | (4-methyl)phenyl | —C≡C— | H | Et |
| 22 | O¹ | — | (4-methyl)phenyl | —C≡C— | H | H |
| 24 | H | H | (4-methyl)phenyl | —CO—NH— | H | Et |
| 25 | H | H | (4-methyl)phenyl | —CO—NH— | H | H |

¹The $X_1$* and $X_2$* symbols jointly represent an oxo group.

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will eral ways in which amides, esters and thioesters are normally prepared. For example, the carboxylic acids of Formula 9 can be activated to form an acid chloride or an activated ester which is thereafter reacted with the amines, alcohols or thioalcohols of the above formulas. More advantageously, however, the formation of the amides, esters or thioesters of the Formulas 10–12 is performed by condensation of the carboxylic acid of Formula 9 with the amines, alcohols or thiols in a suitable aprotic solvent, such as pyridine, in the presence of a condensing agent such as dicyclohexylcarbodiimide (DCC) or more preferably 1-(3-dimethylaminopropyl)-3-ethylcarbodiimidehydrochloride (EDCl). The amide derivatives of Formula 10 can be readily converted to the thioamides of Formula 13 by reaction with [2,4-bis(4-methoxyphenyl)-1,3-dithia-2,4-diphosphetane-2, 4-disulfide] (Lawesson's reagent). The amide derivatives of Formula 10 where the symbol B represents an ester function (such as COOEt) can be readily saponified by treatment with aqueous base, for example LiOH, to yield the corresponding amide derivatives where B represents a free carboxylic acid or its salt. Similar saponification of the esters of Formula 11, or of the thioesters of Formula 12, however is problematic because of the lability of the internal ester and thioester functions. The free acids of these derivatives (where B is COOH or a salt thereof) can be obtained by hydrogenation of the corresponding benzyl esters in which B represents $COOCH_2C_6H_5$.

Reaction Scheme 4

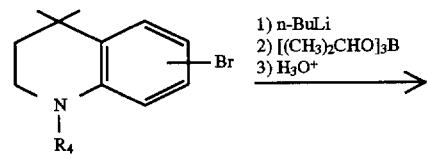

Formula 3

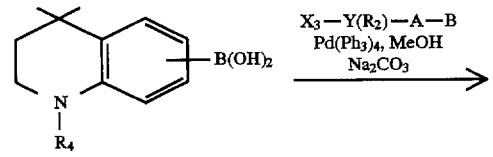

Formula 14

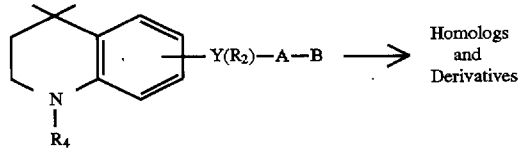

Formula 15

Reaction Scheme 4 discloses a synthetic process for preparing compounds of the invention where, with reference to Formula 1, the Z group is —$(CR_1=CR_1)_n$,— and n' is 0. In other words, this is a reaction scheme for obtaining compounds of the invention where the —$Y(R_2)$—A—B moiety is directly linked to the 6 or 7 position of the N-aryltetrahydroquinoline moiety. Pursuant to this reaction scheme the N-aryl tetrahydrobromoquinoline compounds of Formula 3 are reacted with n-butyl lithium and subsequently with triisopropylborate to provide the boronic acid derivative intermediates of Formula 14. The boronic acid derivatives of Formula 14 react with compounds of the formula $X_3$—$Y(R_2)$—A—B (where the symbols are defined as above and $X_3$ is preferably bromine) in the presence of tetrakis[triphenylphosphine]palladium [$Pd(PPh_3)_4$] and a base, such as sodium carbonate, to yield compounds of Formula 15. Examples of preferred reagents of formula $X_3$—$Y(R_2)$—A—B are ethyl 6-bromo-2-naphthoate, ethyl 4-iodobenzoate, ethyl 6-iodonicotinate, ethyl 2-iodofuran-5-carboxylate, and ethyl 2-iodothiophen-5-carboxylate. The compounds of Formula 15 can be converted into further compounds of the invention by the reactions described above, such as saponification, amide formation, homologation and the like.

Reaction Scheme 5

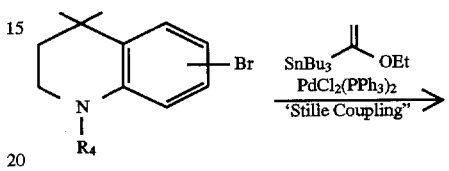

Formula 3

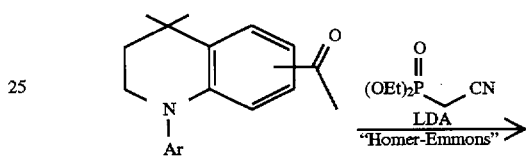

Formula 16

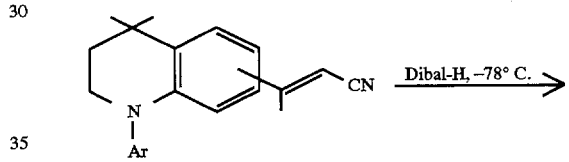

Formula 17

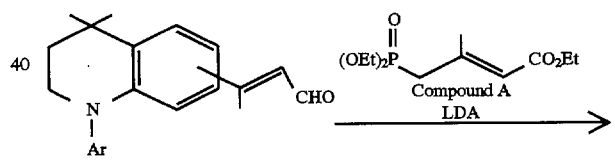

Formula 18.

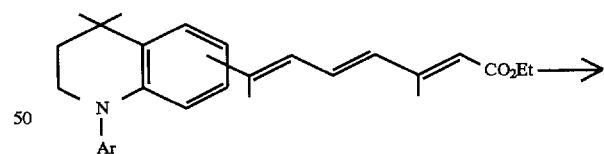

Formula 19

Homologs and Derivatives

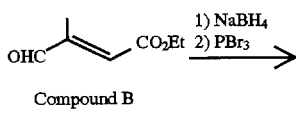

Compound B

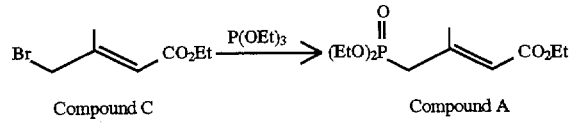

Compound C        Compound A

Reaction Scheme 5 discloses a synthetic route for the preparation of compounds where, with reference to Formula 1, Z is —(CR$_1$=CR$_1$)$_n$—, n' is 3 and the B group is directly attached to the Z group. Thus, in accordance with this scheme the N-aryl tetrahydrobromoquinoline compounds of Formula 3 are reacted with (1-ethoxyvinyl)tributyltin in the presence of bis(triphenylphosphine)palladium(II) chloride to introduce the acetyl group into the 6 or 7 position of the N-aryltetrahydroquinoline nucleus and yield the ketone compounds of Formula 16. The latter reaction is known in the art as a Stille coupling. The ketone compounds of Formula 16 are then reacted in a Horner Emmons reaction, in the presence of strong base such as lithium diisopropylamide (LDA), with diethylcyanomethyl phosphonate. The latter reagent is commercially available. The product of the Horner Emmons reaction is an N-aryltetrahydroquinoline derivative of Formula 17 that is substituted in the 6 or 7 position with a 1-methyl-2-cyanoethenyl group. Those skilled in the art will readily understand that instead of a Horner Emmons reaction the compounds of Formula 17 can also be obtained as a result of an analogous Wittig reaction.

Referring still to Reaction Scheme 5, the cyano function of the compounds of Formula 17 is reduced with a mild reducing agent, such as diisobutylaluminum hydride (Dibal-H) to provide the aldehyde compounds of Formula 18. Another Horner Emmons reaction performed on the aldehydes of Formula 18 with the reagent diethyl(E)-3-ethoxycarbonyl-2-methylallylphosphonate (Compound A) provides compounds of Formula 19 which are within the scope of the present invention. It will be readily apparent to those skilled in the art that the herein described exemplary synthetic process can be readily adapted or modified by utilizing analogous phosphonate or phosponium salt reagents in Horner Emmons or Wittig reactions, respectively, to obtain additional compounds within the scope of Formula 1 in which Z is —(CR$_1$=CR$_1$,—, and n' is 3–5. The compounds of Formula 19 can be converted into further compounds within the scope of the invention by reactions such as saponification, amide formation, reduction to the aldehyde or alcohol stage, and the like. This is indicated in the reaction scheme by conversion to "homologs and derivatives".

Reaction Scheme 5 also discloses the process of preparing the reagent of Compound A, starting from the commercially available ethyl (Z)-3-formyl-2-butenoate (Compound B). In this preparation the aldehyde function of Compound B is reduced with sodium borohydride, and the resulting primary alcohol is reacted with phosphorous tribromide. The resulting ethyl (Z)-3-bromo-2-butenoate (Compound C) is reacted with triethyl phosphonate to give the reagent of Compound A.

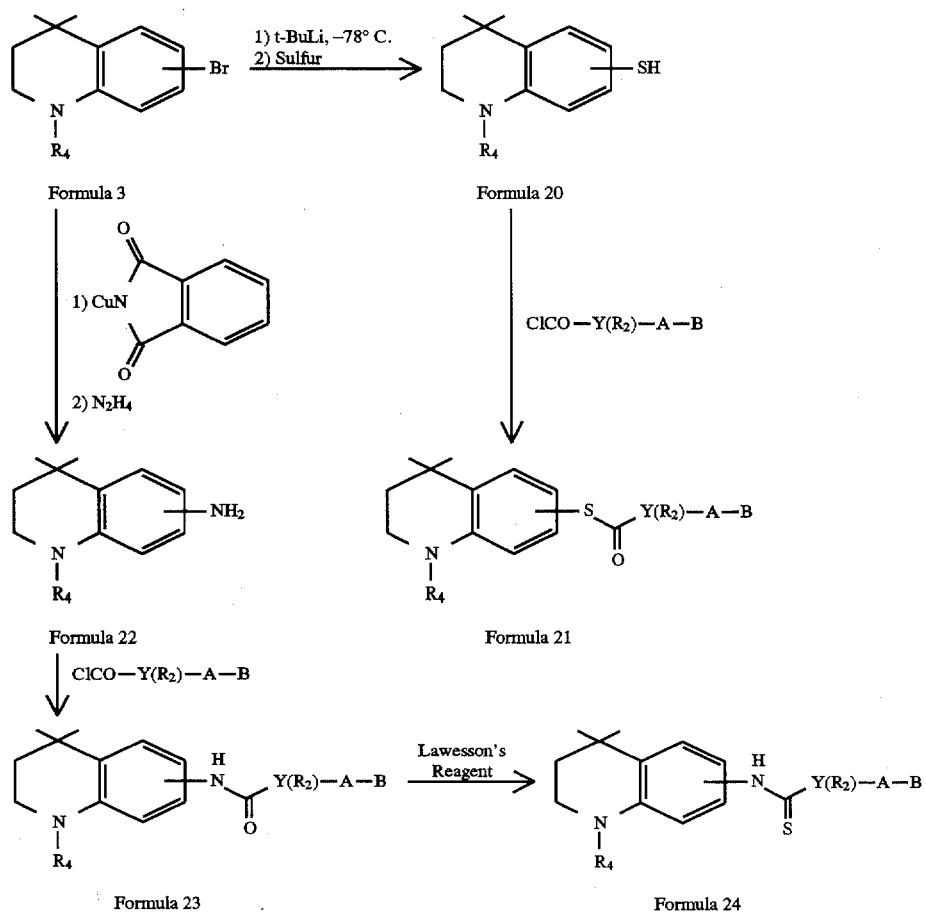

Reaction Scheme 6

-continued
Reaction Scheme 6

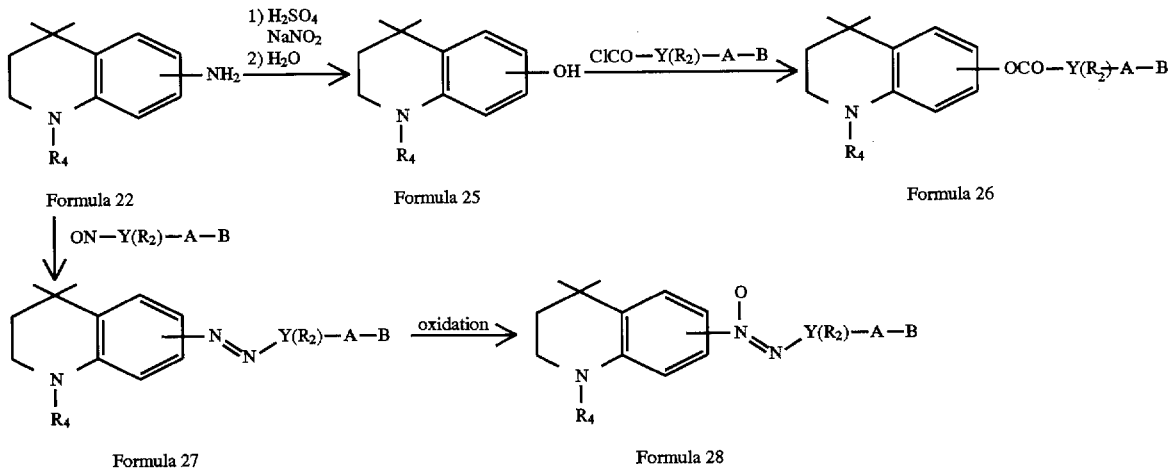

Formula 22     Formula 25     Formula 26

Formula 27     Formula 28

Synthetic routes for the preparation of compounds of Formula 1 where the Z is —SCO— (thioester), —NHCO— (amide) —NHCS— (thioamide) —OCO— (ester) of the order "reverse" to the one described in connection with Reaction Scheme 3, as well as where Z is —N=N— (azo) and —N=N(=O)— (azoxide) are disclosed in Reaction Scheme 6. As is shown in the scheme, the N-aryl tetrahydrobromoquinoline compounds of Formula 3 are reacted with t-butyl lithium, and thereafter with sulfur to provide the 6- or 7-thio- N-aryl tetrahydroquinoline compounds of Formula 20. The thiol compounds of Formula 20 are reacted with a carboxylic acid, or an activated form of the carboxylic acid which forms a thioester and introduces the —CO—Y($R_2$)—A—B moiety into the molecules. Those skilled in the art will understand that just as it is described in connection with the amide, ester and thioester formations in Reaction Scheme 3, various activated forms of carboxylic acids are suitable for this purpose. The instant reaction scheme illustrates the presently preferred method of using acid chlorides of the formula ClCO—Y($R_2$)—A—B in these reactions. Examples for the acid chlorides of formula ClCO—Y($R_2$)—A—B are $ClCOC_6H_4COOEt$ $ClCOC_6H_4COOCH_2C_6H_5$ (the monochlorides of terephthalic acid ethyl and benzyl esters), and $ClCOC_5NH_3COOEt$ and $ClCOC_5NH_3COOCH_2C_6H_5$ (the monochlorides of pyridine 3,6,-dicarboxylic acid ethyl and benzyl esters). The thioesters of Formula 21 are within the scope of the present invention. In order to obtain compounds within the scope of Formula 21 where the B group is a free carboxylic acid (or salt thereof), the thioester is prepared first where the B group is —$COOCH_2C_6H_5$. The benzyl group is then removed by hydrogenation to provide the free acid.

As is shown further in Reaction Scheme 6, the N-aryl tetrahydrobromoquinoline compounds of Formula 3 are reacted with the cuprous salt of phthalimide and therafter with hydrazine to provide the 6- or 7-amino N-aryl tetrahydroquinoline compounds of Formula 22. These are reacted with the acid chlorides of formula ClCO—Y($R_2$)—A—B to yield the amides of Formula 23. The amides of Formula 23 are converted into thioamides of Formula 24 by treatment with [2,4-bis(4-methoxyphenyl)-1,3-dithia-2,4-diphosphetane-2,4-disulfide] (Lawesson's reagent). The amides and thioamides of Formulas 23 and 24 can be subjected to transformations (including saponification of an ester group when B is $COOR_8$) to yield further compounds within the scope of the present invention.

Referring still to Reaction Scheme 6, the 6- or 7-amino N-aryl tetrahydroquinoline compounds of Formula 22 are converted to diazonium salt and thereafter to 6- or 7-hydroxyl N-aryl tetrahydroquinoline compounds of Formula 25. The hydroxyl compounds of Formula 25 are then converted into esters of Formula 26 by reaction with the acid chlorides of the formula ClCO—Y($R_2$)—A—B, or with other activated forms of the carboxylic acids of the general formula HOCO—Y($R_2$)—A—B. As it is described in connection with Reaction Scheme 3, the ester formation may be affected with the free carboxylic acid in an aprotic solvent, such as pyridine, in the presence of dicyclohexylcarbodiimide (DCC) or more preferably 1-(3-dimethylaminopropyl)-3-ethylcarbodiimidehydrochloride (EDCl).. Just like in the case of the above-described thioesters, in order to obtain free carboxylic acids within the scope of Formula 26 (compounds where B is COOH or a salt therof) the benzyl ester (B=$COOCH_2C_6H_5$) is prepared first, and the benzyl protecting group is thereafter removed by hydrogenation.

In order to obtain compounds of Formula 1 where the Z group is —N=N— (azo) or —N(O)=N— (azoxy) the 6- or 7-amino N-aryl tetrahydroquinoline compounds of Formula 22 are reacted with nitroso compounds of the formula ON—Y($R_2$)—A—B. Examples for reagents of formula ON—Y($R_2$)—A—B are ethyl 4-nitrosobenzoate, ethyl 6-nitroso-2-naphthoate, ethyl 4-nitrosobenzoate, ethyl 6-nitroso-nicotinate, ethyl 2-nitroso-furan-5-carboxylate, and ethyl 2-nitroso-thiophen-5-carboxylate. The azo compounds of Formula 27 can be converted to the azoxy compounds of Formula 28 by oxidation with oxidizing agents known in the art, for example with meta-chloroperoxybenzoic acid (MCPBA).

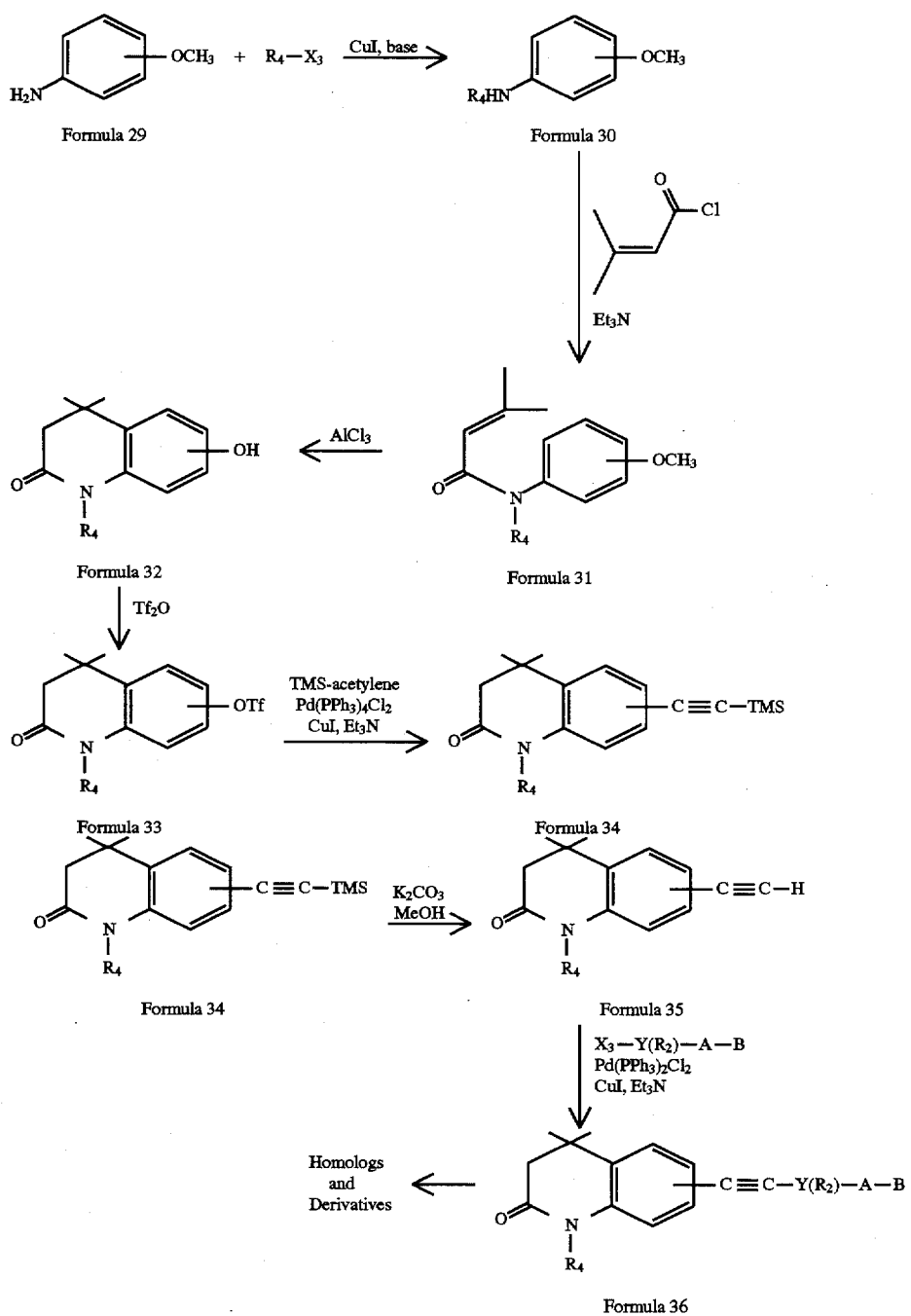

Reaction Scheme 7

Reaction Scheme 7 discloses a synthetic process for the preparation of compounds of the invention where, with reference to Formula 1 $X_1$ and $X_2$ jointly symbolize an oxo (=O) group. Whereas the scheme discloses an example where the $R_1$ groups are methyl, there are no $R_2$ and $R_3$ subtituents (other than hydrogen) and the Z group is ethynyl (—C≡C—), nevertheless the synthetic route can be readily adapted within the generic principles disclosed above for the preparation of additional compounds of the invention which have additional substituents within the scope of Formula 1.

The synthetic process starts with known and commercially available 3 or 4-methoxyaniline. Presently the process is preferably carried out with 3-methoxyaniline which gives rise to 7-substituted N-aryl tetrahydroquinolines. The starting material, 3 or 4-methoxyaniline, is reacted with an arylating agent of the formula $R_4$—$X_3$ where $X_3$ is a leaving group, preferably halogen and even more preferably iodine. Preferred examples for the reagent $R_4$—$X_3$ are 4-iodotoluene and iodobenzene. Other examples are 4-ethyliodobenzene, dimethyliodobenzene, 4-fluoroiodobenzene, 4-nitroiodobenzene, ethyl 4-iodobenzoate, 6-iodopyridine, 5-iodofuran, and 5-iodothiophene. The reactions between the methoxyanilines of formula 29 and $R_4$—$X_3$ are preferably conducted at elevated temperature, in the presence of an acid acceptor and copper(I)iodide catalyst and provide the N-aryl methoxyanilines of Formula 30. The N-aryl methoxyanilines of Formula 30 are reacted with 3,3-dimethylacryloyl chloride to yield the amides of Formula 31 which are subsequently subjected to a cyclization reaction under Friedel Crafts conditions to provide 6- or 7-hydroxy N-aryl tetrahydroquinolin-2-ones of Formula 32. The cyclization reaction may give rise to positional isomers (not shown in the reaction scheme) which are separated by known methods (such as chromatography) to provide the desired 6- or 7-hydroxy substituted tetrahydroquinolin-2-one derivatives. The 6- or 7-hydroxy N-aryl tetrahydroquinolin-2-ones of Formula 32 are then converted to the trifluoromethylsulfonyl (triflate) derivatives of Formula 33 by treatment with trifluoromethylsulfonyl anhydride and the triflate derivative is reacted with (trimethylsilyl)acetylene in the presence of copper(I)iodide, triethylamine and bis(triphenylphosphine) palladium(II) chloride to yield N-aryl 6 or 7 -[(trimethylsilyl)ethynyl]quinolin-2-one derivatives of Formula 34. The N-aryl [(trimethylsilyl)ethynyl]quinolin-2-one derivatives of Formula 34 are thereafter subjected to the sequence of reactions described in Reaction Scheme 1 for the N-aryl [(trimethylsilyl)ethynyl]quinoline derivatives of Formula 4. The products of these reactions, shown in Reaction Scheme 7, are the compounds of Formula 36 within the scope of the present invention.

SPECIFIC EXAMPLES

N-(3-Bromophenyl)-3,3-dimethylacrylamide

To a suspension of NaH (4.15 g, 173 mmol, 60% in oil) in 50 ml of THF was cannulated a solution of 20.322 g (118 mmol) of 3-bromo-aniline in 50 ml of THF. The resulting mixture was stirred at 0° C. for 45 min and warmed to room temperature over a period of 15 min. To this solution was added through cannulation 13.123 g (173 mmol) of 3,3-dimethylacryloyl chloride. The mixture was stirred at room temperature for 24 h and thereafter slowly poured into ice water. The resulting mixture was extracted with methylene chloride (twice), dried over MgSO$_4$ and concentrated to yield a solid. The solid was purified by recrystallization in hexane/EtOAc (2:1) to give the title compound as a light brown solid. PNMR (CDCl$_3$) d 7.83 (1H, b), 7.30 (4H, m), 5.68 (1H, s), 2.22 (3H, s), 1.90 (3H, s).

7-bromo-3,4-dihydro-4,4-dimethyl-2(1H)-quinilinone

Into a 500 ml round-buttom flask was placed 13.52 g (101 mmol) of AlCl$_3$ under nitrogen purge and kept at 0° C. Thereafter, 22.41 g of N-(3-bromophenyl)-3,3-dimethylacrylamide in 350 ml CH$_2$Cl$_2$ was slowly added by syringe. The reaction mixture was stirred at 0° C. for 72 h, and thereafter slowly quenched with small chunks of icecubes and finally with water. The aqueous layer was washed with CH$_2$Cl$_2$ and the organic layer was dried over Na$_2$SO$_4$. The solvent was evaporated and the residue purified by recrystallization from EtOAc—hexane to give the title compound as off-white solids. PNMR (CDCl$_3$) d 8.87 (1H, b), 7.23 (1H, d, J=7.95 Hz), 7.16 (2H, s), 7.0 (1H, s), 2.49 (2H, s), 1.32 (6H, s).

4,4-dimethyl-1,2,3,4-tetrahydro-7-bromoquinoline

To a solution of 3.20 g (12.6 mmol) of 7-bromo-3,4-dihydro-4,4-dimethyl-2(1H)-quinilinone in 35 mL of tetrahydrofuran stirring at 0° C. under argon, was added 17 mL (17 mmol, 1M in ether) of lithium aluminumhydride. The resulting solution was stirred at 0° C. to room temperature for 19 hours. The reaction was cooled, and carefully poured onto ice (250 mL v:v) saturated sodium tartrate was added and the mixture extracted with ether (2x). The combined organic layers were then dried (MgSO$_4$), and filtered and concentrated in-vacuo to give the title compound as an oil (2.81 g, 93%):

$^1$H NMR (300 MHz, CDCl$_3$) δ 1.26 (6 H, s), 1.71 (2 H, t, J=5.9 Hz), 3.30 (2 H, t, J=5.9 Hz), 3.94 (1 H, s, NH), 6.59 (1 H, d, J=1.9 Hz), 6.71 (1 H, dd, J=8.2, 1.9 Hz), 7.01 (1 H, d, J=8.2 Hz). 4,4-Dimethyl-1,2,3,4-tetrahydro-N-(4-methylphenyl)-7-bromoquinoline (Compound 1)

To a solution of 0.22 g (0.91 mmol) of 4,4-dimethyl-1,2,3,4-tetrahydro-7-bromoquinoline and 5.50 g (25 mmol) of 4-iodotoluene warmed to 50° C. under argon, was added 0.16 g (1.9 mmol) of potassium carbonate and 0.098 g (0.51 mmol) of copper(I) iodide. The resulting mixture was heated at 185° C. for 96 h. The reaction was cooled to room temperature, water was added, and the mixture was extracted twice with methylene chloride. The combined organic layers were then washed with brine, dried (Na$_2$SO$_4$), filtered and concentrated in vacuo to give an oil. The mixture was purified by flash chromatography (hexanes) to give the title compound as a clear oil. PNMR (300 MHz, CDCl$_3$): d 1.32 (6 H, s), 1.82 (2 H, t, J=6.0 Hz), 2.36 (3 H, s), 3.57 (2 H, t, J=6.0 Hz), 6.68 (1 H, d, J=2.1 Hz), 6.77 (1 H, dd, J=8.2, 2.1 Hz), 7.07 (1 H, d, J=8.2 Hz), 7.10 (2 H, d, J=8.3 Hz), 7.19 (1 H, d, J=8.3 Hz).

4,4-Dimethyl-1,2,3,4-tetrahydro-N-(4-methylphenyl)-7-[2-(trimethylsilyl)ethynyl]quinoline (Compound 2)

To a solution of 0.20 g (0.6 mmol) of 4,4-dimethyl-1,2, 3,4-tetrahydro-N-(4-methylphenyl)-7-bromoquinoline (Compound 1) in 2.90 g (4.0 mL, 29 mmol) of triethylamine were added 0.030 g (0.16 mmol) of copper(I) iodide, 0.35 g (0.50 mL, 3.5 mmol) of (trimethylsilyl)acetylene and 0.074 g (0.11 mmol) of bis(triphenylphosphine)palladium(II) chloride. The resulting mixture was heated at 75° C. for 20 hours. The reaction mixture was cooled, methylene chloride was added and the mixture was adsorbed onto silica gel. The mixture was separated by flash chromatography (hexanes) to give the title compound as a yellow solid. PNMR (300 MHz, CDCl,) d 0.20 (9 H, s), 1.35 (6 H, s), 1.84 (2 H, t, J=6.0 Hz), 2.39 (3 H, s), 3.59 (2 H, t, J=6.0 Hz), 6.78 (1 H, d, J=1.7 Hz), 6.84 (1 H, rid, J=7.8,1.7 Hz), 7.12–7.17 (5 H, several overlapping d's).

4,4-Dimethyl-1,2,3,4-tetrahydro-N-(4-methylphenyl)-7-ethynylquinoline (Compound 3)

To a solution of 0.18 g (0.52 mmol) of 4,4-dimethyl-1,2, 3,4-tetrahydro-N-(4-methylphenyl)-7-[2-(trimethylsilyl) ethynyl]quinoline (Compound 2) in 12.0 mL of methanol and 1.0 mL of tetrahydrofuran was added 0.088 g (0.64 mmol) of potassium carbonate, and the resulting mixture was stirred at room temperature for 6 hours and at 30° C. for 1 hour. The mixture was concentrated in vacuo, water was added, and the mixture was extracted with diethyl ether (2x). The combined organic layers were washed with brine, dried (MgSO4), filtered, and concentrated in vacuo to give the title compound as an orange oil. PNMR (300 MHz, CDCl$_3$): d 1.34 (6 H, s), 1.83 (2 H, t, J=6.0 Hz), 2.35 (3 H, s), 2.86 (1 H, s), 3.56 (2 H, t, J=6.0 Hz), 6.73 (1 H, d, J=1.6 Hz), 6.82 (1 H, dd, J=7.9, 1.6 Hz), 7.11 (2 H, d, J=8.4 Hz), 7.17 (1 H, J=7.9 Hz), 7.18 (2 H, d, J=8.4 Hz).

Ethyl 4-(2-(4,4-Dimethyl-1,2,3,4-tetrahydro-N-(4-methylphenyl)quinolin-7 -yl)ethynyl)benzoate (Compound 4)

To a mixture of 0.13 g (0.47 mmol) of 4,4-dimethyl-1,2, 3,4-tetrahydro-N-(4-methylphenyl)-7-ethynylquinoline (Compound 3) and 0.25 g (0.91 mmol) of ethyl 4-iodobenzoate were added 2.9 g (4.0 mL, 29 mmol) of triethylamine, 0.025 g (0.13 mmol) of copper(I)iodide, and 0.077 g (0.11 mmol) of bis(triphenylphosphine)palladium (II) chloride, consecutively. The resulting mixture was stirred at room temperature for 96 hours. Methylene chloride was added and the reaction mixture was adsorbed onto silica gel. The mixture was purified by flash chromatography (2% ethyl acetate in hexanes) to give the title compound as an ivory solid. PNMR (300 MHz, CDCl$_3$) d 1.36 (6 H, s), 1.39 (3 H, t, J=7.1 Hz), 1.85 (2 H, t, J=6.0 Hz), 2.37 (3 H, s), 3.60 (2 H, t, J=6.0 Hz), 4.36 (2 H, q, J=7.1 Hz), 6.78 (1 H, d, J=1.7 Hz), 6.87 (1 H, dd, J=8.0, 1.7 Hz), 7.14 (2 H, d, J=8.4 Hz), 7.22 (2 H, d, J=8.4 Hz), 7.23 (1 H, d, J=8.0 Hz), 7.48 (2 H, d, J=8.4 Hz), 7.97 (2 H, d, J=8.4 Hz).

4-(2-(4,4-Dimethyl-1,2,3,4-tetrahydro-N-(4-methylphenyl)quinolin-7-yl)ethynyl)benzoic Acid (Compound 5)

To a solution of ethyl 4-(2-(4,4-dimethyl-1,2,3,4-tetrahydro-N-(4-methylphenyl)quinolin-7-yl)ethynyl)benzoate (Compound 4) (0.105 g, 0.25 mmol) in 10.0 mL of tetrahydrofuran and 0.5 mL of methanol was added 1.0 mL (1.5 mmol) of 1.5M aqueous LiOH. The resulting solution was stirred at room temperature for 24 hours. The mixture was concentrated in vacuo, water was added, and the mixture was extracted with ethyl acetate (2x). The combined organic layers were washed with brine, dried (MgSO$_4$), filtered, and concentrated in vacuo to give the title compound as a yellow solid, which was recrystallized from 2:1 acetonitrile:ethyl acetate to give yellow needles. PNMR (300 MHz, DMSO) d 1.31 (6 H, s), 1.80 (2 H, t, J=5.9 Hz), 2.31 (3 H, s), 3.53 (2 H, t, J=5.9 Hz), 6.50 (1 H, d, J=1.6 Hz), 6.83 (1 H, dd, J=8.0, 1.6 Hz), 7.16 (2 H, d, J=8.4 Hz), 7.25 (2 H, J=8.4 Hz), 7.29 (1 H, d, J=8.0 Hz), 7.55 (2 H, d, J=8.4 Hz), 7.89 (2 H, d, J=8.4 Hz)

4,4-Dimethyl-1,2,3,4-tetrahydro-N-phenyl-7-bromoquinoline (Compound 6)

To a solution of 0.19 g (0.78 mmol) of 4,4-dimethyl-1,2,3,4-tetrahydro-7-bromoquinoline and 5.5 g (3.0 mL, 27 mmol) of 4-iodobenzene stirring under argon, were added 0.30 g (2.2 mmol) of potassium carbonate and 0.12 g (0.63 mmol) of copper(I) iodide. The resulting mixture was heated at 185° C. for 96 hours. The reaction was cooled to room temperature, water was added, and the mixture was extracted with methylene chloride (2x). The combined organic layers were washed with brine, dried (Na$_2$SO$_4$), filtered, and concentrated in vacuo to give an oil. The residue was purified by flash chromatography (hexanes) to give the product as a clear oil. PNMR (300 MHz, CDCl$_3$) d 1.33 (6 H, s), 1.84 (2 H, t, J=6.1 Hz), 3.62 (2 H, t, J=6.1 Hz), 6.77 (1 H, d, J=2.0 Hz), 6.81 (1 H, dd, J=8.2, 2.0 Hz), 7.10 (1 H, d, J=8.2 Hz), 7.16–7.23 (3 H, m), 7.39 (2 H, 2 doublets overlapping).

4,4-Dimethyl-1,2,3,4-tetrahydro-N-phenyl-7-[2-(trimethylsilyl) ethynyl]quinoline (Compound 7)

To a solution of 0.10 g (0.32 mmol) of 4,4-dimethyl-1,2,3,4-tetrahydro-N-phenyl-7-bromoquinoline (Compound 6) and 5.0 g (4.0 mL, 36 mmol) triethylamine were added 0.032 g (0.17 mmol) of copper(I) iodide, 0.70 g (1.0 mL, 7.1 mmol) of (trimethylsilyl)acetylene, and 0.050 g (0.07 mmol) of bis(triphenylphosphine)palladium(I$_D$ chloride. The resulting mixture was heated at 70° C. for 22 hours. The reaction was cooled, methylene chloride was added, and the mixture was adsorbed onto silica gel. The mixture was purified by flash chromatography (hexanes) to give the title compound as a yellow solid. PNMR (300 MHz, CDCl$_3$) d 0.17 (9 H, s), 1.32 (6 H, s), 1.82 (2 H, t, J=6.0 Hz), 3.61 (2 H, t, J=6.0 Hz), 6.85 (2 H, overlapping d's), 7.15–7.41 (6 H, m).

4,4-Dimethyl-1,2,3,4-tetrahydro-N-phenyl-7-ethynylquinoline (Compound 8)

To a solution of 0.050 g (0.15 mmol) of 4,4-dimethyl-1,2,3,4-tetrahydro-N-phenyl-7-[2-(trimethylsilyl)ethynyl] quinoline (Compound 7) in 4.0 mL of methanol was added 0.032 g (0.23 mmol) of potassium carbonate, and the resulting mixture was stirred at room temperature for 20 hours. The mixture was then concentrated in vacuo, water was added, and the mixture was extracted with diethyl ether (2x). The organic layers were washed with brine, dried (Na$_2$SO$_4$), filtered, and concentrated in vacuo to give the title compound as an oil. PNMR (300 MHz, CDCl$_3$) d 1.34 (6 H, s), 1.84 (2 H, t, J=6.0 Hz), 2.88 (1 H, s), 3.62 (2 H, t, J=6.0 Hz), 6.82 (1 H, d, J=1.6 Hz), 6.85 (1 H, rid, J=7.9, 1.6 Hz), 7.13–7.39 (6 H, m).

Ethyl 4-(2-(4,4-Dimethyl-1,2,3,4-tetrahydro-N-phenylquinolin-7-yl)ethynyl)benzoate (Compound 9)

To a mixture of 0.020 g (0.08 mmol) of 4,4-dimethyl-1,2,3,4-tetrahydro-N-phenyl-7-ethynylquinoline (Compound 8) and 0.51 g (1.8 mmol) of ethyl 4-iodobenzoate were added 1.5 g (2.0 mL, 14 mmol) of triethylamine, 6.2 mg( 0.03 mmol) of copper(I)iodide, and 12 mg (0.02 mmol) of bis(triphenylphosphine)palladium(II) chloride, consecutively. The resulting mixture was heated at 40° C. for 5.5 hours. The reaction was cooled, methylene chloride was added, and the reaction mixture was adsorbed onto silica gel. The mixture was purified by flash chromatography (5% ethyl acetate in hexanes) to give the title compound as a yellow oil. PNMR (300 MHz, CDCl$_3$) d 1.36 (6 H, s), 1.39 (3 H, t, J=7.2 Hz), 1.86 (2 H, t, J=6.0 Hz), 3.64 (2 H, t, J=6.0 Hz), 4.36 (2 H, q, J=7.2 Hz), 6.87 (1 H, d, J=1.6 Hz), 6.91 (1 H, dd, J=7.9, 1.6 Hz), 7.14 (1 H, t, J=7.3 Hz), 7.25 (1 H, d, J=7.9 Hz), 7.25 (2 H, d, J=7.3 Hz), 7.39 (2 H, t, J=7.3 Hz), 7.48 (2 H, d, J=8.5 Hz), 7.97 (2 H, d, J=8.5 Hz).

4-(2-(4,4-Dimethyl-1,2,3,4-tetrahydro-N-phenylquinolin-7-yl)ethynyl)benzoic Acid (Compound 10)

To a solution of 8.7 mg (0.02 mmol) of ethyl 4-(2-(4,4-dimethyl-1,2,3,4-tetrahydro-N-phenylquinolin-7-yl) ethynyl)benzoate (Compound 9) in 1.0 mL in tetrahydrofuran was added 0.5 mL (0.1 mmol) of 0.2M aqueous LiOH. The resulting solution was stirred at room temperature for 20 hours. The mixture was then concentrated in vacuo. Water was added, and the mixture was extracted with ethyl acetate (2x). The combined organic layers were washed with brine, dried (MgSO$_4$), filtered, and concentrated in vacuo to give the title compound as a yellow solid. PNMR (300 MHz, DMSO) d 1.31 (6 H, s), 1.81 (2 H, t, J=5.9 Hz), 3.58 (2 H, t, J=5.9 Hz), 6.61 (1 H, s), 6.87 (1 H, d, J=8.0 Hz), 7.19 (1 H, t, J=7.1 Hz), 7.26–7.33(3 H, m), 7.43 (2 H, t, J=7.1 Hz), 7.55 (2 H, d, J=8.2 Hz), 7.89 (2 H, d, J=8.2 Hz).

Ethyl 4-(2-(4,4-Dimethyl-1,2,3,4-tetrahydro-N-(4-methylphenyl)quinolin-7-yl)ethynyl)-2-fluorobenzoate (Compound 11)

To a mixture of 0.20 g (0.72 mmol) of 4,4-dimethyl-1,2,3,4-tetrahydro-N-(4-methylphenyl)-7-ethynylquinoline (Compound 3) and 0.39 g (1.5 mmol) of ethyl 2-fluoro-4-iodobenzoate were added 2.9 g (4.0 mL, 29 mmol) of triethylamine, 0.029 g (0.15 mmol) of copper(I) iodide, and 0.113 g (0.16 mmol) of bis(triphenylphosphine)palladium (II) chloride, consecutively. The resulting mixture was stirred at room temperature for 20 hours. Methylene chloride was added and the reaction was adsorbed onto silica gel. The product was obtained by flash chromatography (5% ethyl acetate in hexanes) followed by recrystallization in ethanol to give the title compound as orange crystals. PNMR (300 MHz, CDCl$_3$) d 1.37 (6 H, s), 1.40 (3 H, t, J=7.1 Hz), 1.86

(2 H, t, J=6.0 Hz), 2.38 (3 H, s), 3.61 (2 H, t, J=6.0 Hz), 4.39 (2 H, q, J=7.1 Hz), 6.77 (1 H, d, J=1.7 Hz), 6.87 (1 H, dd, J=7.9, 1.7 Hz), 7.23–7.28 (7 H, m), 7.86 (1 H, t, J=7.8 Hz).

4-(2-(4,4-Dimethyl-1,2,3,4-tetrahydro-N-(4-methylphenyl)quinolin-7-yl)ethynyl)-2-fluorobenzoic Acid (Compound 12)

To a solution of 0.088 g (0.19 mmol) of ethyl 4-(2-(4,4-dimethyl-1,2,3,4-tetrahydro-N-(4-methylphenyl) quinolin-7-yl)ethynyl)-2-fluorobenzoate (Compound 11) in 3.0 mL of tetrahydrofuran and 0.5 mL of methanol was added 0.5 mL (0.5 mmol) of 1.0M aqueous LiOH. The resulting solution was stirred at room temperature for 72 hours. The mixture was concentrated in vacuo, water was added, and the mixture was extracted with ethyl acetate (2x). The combined organic layers were washed with brine, dried (MgSO₄), filtered, and concentrated in vacuo. The residue was purified by recrystallization from acetonitrile to give the title compound as a solid (77 mg, 90%). PNMR (300 MHz, d6-acetone) d 1.36 (6 H, s), 1.40 (3 H, t, J=7.1 Hz), 1.86 (2 H, t, J=5.9 Hz), 2.34 (3 H, s), 3.62 (2 H, t, J=5.9 Hz), 6.64 (1 H, d, J=1.6 Hz), 6.86 (1 H, dd, J=8.0, 1.6 Hz), ), 7.17 (2 H, d, J=8.3 Hz), 7.25–7.37 (5 H, m), 7.92 (1 H, t, J=7.8 Hz).

Ethyl (E)-4-(2-(4,4-Dimethyl-1,2,3,4-tetrahydro-N-(4-methylphenyl)quinolin-7-yl)ethenyl)-benzoate (Compound 13)

To a mixture of 0.081 g (0.24 mmol) of 4,4-dimethyl-1,2,3,4-tetrahydro-N-(4-methylphenyl)-7-bromoquinoline (Compound 1) and 0.092 g (0.52 mmol) of ethyl 4-vinylbenzoate were added 1.4 g (2.0 mL, 14 mmol) of triethylamine, 0.029 g (0.09 mmol) of tris(o-tolyl) phosphine, and 11 mg (0.05 mmol) of palladium(II) diacetate, consecutively. The resulting mixture was heated at 95° C. for 6 hours. Methylene chloride was added, and the reaction mixture was adsorbed onto silica gel. The product was obtained by flash chromatography (5% ethyl acetate in hexanes) followed by recrystallization from ethanol to give the title compound as orange crystals. PNMR (300 MHz, CDCl₃) d 1.37 (6 H, s), 1.39 (3 H, t, J=7.1 Hz), 1.86 (2 H, t, J=5.9 Hz), 2.38 (3 H, s), 3.62 (2 H, t, J=5.9 Hz), 4.36 (2 H, q, J=7.1 Hz), 6.78–7.28 (9 H, m), 7.46 (2 H, d, J=8.4 Hz), 7.96 (2 H, d, J=8.4 Hz).

(E)-4-(2-(4,4-dimethyl-1,2,3,4-tetrahydro-N-(4-methylphenyl)quinolin-7-yl)ethenyl)benzoic acid (Compound 14)

To a solution of 0.033 g (0.08 mmol) of ethyl (E)-4-(2-(4,4-dimethyl-1,2,3,4-tetrahydro-N-(4-methylphenyl) quinolin-7-yl)ethenyl)benzoate (Compound 13) in 4.0 mL of tetrahydrofuran and 1.0 mL of methanol was added 1.0 mL (0.6 mmol) of 0.6M aqueous LiOH. The resulting solution was stirred at room temperature for 48 hours. The mixture was concentrated in vacuo, water was added, and the mixture was extracted with ethyl acetate (2x). The combined organic layers were washed with brine, dried (MgSO₄), filtered, and concentrated in vacuo, followed by recrystallization in acetonitrile to give the title compound as a solid. PNMR (300 MHz, DMSO) d 1.30 (6 H, s), 1.77 (2 H, t, J=6.0 Hz), 2.30 (3 H, s), 3.54 (2 H, t, J=6.0 Hz), 6.69 (1 H, s), 6.95–7.28 (8 H, m), 7.46 (2 H, d, J=8.4 Hz), 7.96 (2 H, d, J=8.4 Hz).

N-(4-Methylphenyl)-3-methoxyaniline (Compound 15)

To a suspension of 0.11 g (4.6 mmol, hexane washed 3 x, 50–60% in oil) sodium hydride in 1.0 mL of hexamethylphosphoramide was cannulated a solution of 0.11 g (0.89 mmol) of 3-methoxyaniline in 2.0 mL hexamethylphosphoramide. The resulting mixture was heated at 55° C. for 20 min. To this was added 0.18 g ( 0.93 mmol) of copper(I) iodide and the mixture was heated at 55° C. for 1.5 hours. 4-iodotoluene was added and the reaction heated at 85° C. for 3 hours. The reaction mixture was allowed to cool to room temperature, hexane was added and the reaction was then loaded onto a silica gel column. The mixture was purified by flash chromatography (100% hexane, 5% ethyl acetate in hexanes) to give the title compound as an orange oil. PNMR (300 MHz, CDCl₃) d 2.30 (3 H, s), 3.76 (3 H, s), 5.65 (1 H, s), 6.43 (1 H, m), 6.57 (1 H, d, J=1.6 Hz), 6.58 (1 H, m), 7.01 (2 H, d, J=8.5 Hz), 7.09 (2 H, d, J=8.5 Hz), 7.15 (1 H, d, J=8.6 Hz).

N-(4-methylphenyl)-N-(3-methoxyphenyl)-3,3-dimethylacrylamide (Compound 16)

To a solution of 0.10 g (0.47 mmol) of N-(4-methylphenyl)-3-methoxyaniline (Compound 15) in 3.0 mL of tetrahydrofuran stirring at 0° C. under argon, were added 0.15 mL (0.11 g, 1.1 mmol) of triethylamine and then 0.19 g (1.6 mmol) of 3,3-dimethylacryloyl chloride. The reaction mixture was allowed to warm to room temperature over 30 minutes and then heated at 50° C. for 13 hours. The reaction mixture was cooled, water was added, and the mixture was extracted with diethyl ether (2x). The combined organic layers were then washed with brine, dried (Na₂SO₄), filtered and concentrated in vacuo to give an oil. The mixture was purified by flash chromatography (10% ethyl acetate in hexanes, 20% ethyl acetate in hexanes) to give the title compound as a yellow oil. PNMR (300 MHz, CDCl₃) d 1.75 (3 H, s), 2.16 (3 H, s), 2.34 (3 H, s), 3.76 (3 H, s), 5.61 (1 H, s), 6.75–6.81 (2 H, m), 7.08 (2 H, d, J=8.5 Hz), 7.14 (2 H, d, J=8.5 Hz), 7.23 (1 H, t, J=7.8 Hz).

4,4-Dimethyl-3,4-dihydro-N-(4-methylphenyl)-7-hydroxy-2(1H)-quinolinone (Compound 17)

To a solution of 55 mg (0.19 mmol) of N-(4-methylphenyl)-N-(3-methoxyphenyl)-3,3-dimethylacrylamide (Compound 16) in 2.0 mL of trichloroethane stirring under argon, was added 0.11 g (0.84 mmol) of aluminum chloride and the mixture was heated at 90°–100° C. for 18 hours. The reaction was cooled, poured onto ice, the mixture extracted with diethyl ether (2x) dried (MgSO₄), filtered and concentrated in vacuo to give an oil. The mixture was purified by flash chromatography (30% ethyl acetate in hexanes) to give the title compound as a white solid (4.0 mg). PNMR (300 MHz, CDCl₃) d 1.37 (6 H, s), 2.41 (3 H, s), 2.65 (2 H, s), 4.76 (1 H, s), 5.92 (1 H, d, J=2.6 Hz), 6.49 (1 H, rid, J=8.3, 2.6 Hz), 7.09 (2 H, d, J=8.1 Hz), 7.17 (1 H, d, J=8.3 Hz), 7.30 (2 H, d, J=8.1 Hz).

4,4-Dimethyl-3,4-dihydro-N-(4-methylphenyl)-7-[(trifluoromethylsulfonyl) oxy]-2(1H)-quinolinone (Compound 18)

To a solution of 0.20 g (0.71 mmol) of 4,4-dimethyl-3,4-dihydro-N-(4-methylphenyl)-7-hydroxy-2(1H)-quinolinone (Compound 17) in 4.0 mL of pyridine stirring at 0° C. under argon, was added 1.0 mL of trifluoromethylsulfonyl anhydride and the reaction was stirred at 0° C. to room temperature for 72 hours. The reaction mixture was quenched by the addition of water, extracted with diethyl ether: ethyl acetate (1:1) (2x). The combined organic layers were washed with 10% HCl until pH=5 was reached, then with water and brine, thereafter dried (Na₂SO₄), filtered and concentrated in vacuo to give an oil. The product was purified by flash chromatography (40% ethyl acetate in hexanes) to give the title compound as a solid. PNMR (300 MHz, CDCl₃) d 1.42 (6 H, s), 2.43 (3 H, s), 2.70 (2 H, s), 6.30 (1 H, d, J=2.6 Hz), 6.93 (1 H, dd, J=8.5, 2.6 Hz), 7.08 (2 H, d, J=8.4 Hz), 7.33 (2 H, d, J=8.4 Hz), 7.38 (1 H, d, J=8.5 Hz).

4,4-Dimethyl-3,4-dihydro-N-(4-methylphenyl)-7-[2-(trimethylsilyl)ethynyl]-2(1H)-quinolinone (Compound 19)

To a solution of 0.20 g (0.57 mmol) of 4,4-dimethyl-3,4-dihydro-N-(4-methylphenyl)-7-[(trifluoromethanesulfonyl)oxy]-2(1H)-quinolinone (Compound 18) in 1.45 g (2.0 mL, 14 mmol) of triethylamine were added 0.70 g (1.0 mL, 7.1 mmol) of (trimethylsilyl)acetylene and 94 mg (0.13 mmol) of bis(triphenylphosphine)palladium(II) chloride. The resulting mixture was heated at 85° C. for 16 h. The reaction mixture was cooled, methylene chloride was added and the mixture adsorbed onto silica gel. The mixture was purified by flash chromatography (25% ethyl acetate in hexanes) to give the title compound as a foam. PNMR (300 MHz, CDCl$_3$) d 0.19 (9 H, s), 1.40 (6 H, s), 2.44 (3 H, s), 2.66 (2 H, s), 6.53 (1 H, d, J=1.4 Hz), 7.09 (2 H, d, J=8.4 Hz), 7.15 (1 H, dd, J=7.9, 1.4 Hz), 7.25 (1 H, d, J=7.9 Hz), 7.33 (2 H, d, J=8.4 Hz).

4,4-Dimethyl-3,4-dihydro-N-(4-methylphenyl)-7-ethynyl-2(1H)-quinolin-2-one (Compound 20)

To a solution of 0.17 g (0.47 mmol) of 4,4-dimethyl-3,4-N-(4-methylphenyl)-7-[2-(trimethylsilyl)ethynyl]-2(1H)-quinolinone (Compound 19) in 4.0 mL of methanol and was added 0.108 g (0.78 mmol) of potassium carbonate and the resulting mixture was stirred at room temperature for 3 hours. The reaction mixture was concentrated in vacuo, water was added, and the mixture was extracted with diethyl ether (2x). The combined organic layers were washed with brine, dried (MgSO$_4$), filtered, and concentrated in vacuo to give the title compound as an oil (0.13 g). PNMR (500 MHz, CDCl$_3$) d 1.41 (6 H, s), 2.42 (3 H, s), 2.66 (2 H, s), 3.80 (1 H, s), 6.55 (1 H, d, J=1.5 Hz), 7.08 (2 H, d, J=8.3 Hz), 7.17 (1 H, dd, J=7.9, 1.5 Hz), 7.28 (1 H, J=7.9 Hz), 7.31 (2 H, d, J=8.3 Hz).

Ethyl 4-(2-(4,4-Dimethyl-3,4-dihydro-N-(4-methylphenyl)-2(1H)-quinolinon-7-yl)ethynyl)benzoate (Compound 21)

To a mixture of 0.13 g (0.45 mmol) of 4,4-dimethyl-3,4-dihydro-N-(4-methylphenyl)-7-ethynyl-2(1H)-quinolinone (Compound 20) and 0.29 g (1.0 mmol) of ethyl 4-iodobenzoate were added 2.9 g (4.0 mL, 29 mmol) of triethylamine, 2.0 mL of dimethylformamide, 0.019 g (0.10 mmol) of copper(I)iodide, and 0.067 g (0.10 mmol) of bis(triphenylphosphine)palladium(II) chloride, consecutively. The resulting mixture was heated at 50° C. for 16 hours. Thereafter methylene chloride was added and the reaction mixture was adsorbed onto silica gel. The mixture was purified by flash chromatography (15% ethyl acetate in hexanes) to give the title compound as an orange solid. PNMR (300 MHz, CDCl$_3$) d 1.41 (3 H, t, J=7.1 Hz), 1.43 (6 H, s), 1.86 (2 H, t, J=6.0 Hz), 2.44 (3 H, s), 2.48 (2 H, s), 4.37 (2 H, q, J=7.1 Hz), 6.59 (1 H, d, J=1.5 Hz), 7.12 (2 H, d, J=8.3 Hz), 7.20–7.38 (4 H, m), 7.50 (2 H, d, J=8.1 Hz), 7.98 (2 H, d, J=8.1 Hz).

4-(2-(4,4-Dimethyl-3,4-dihydro-N-(4-methylphenyl)-2(1H)-quinolinon-7-yl)ethynyl)benzoic Acid (Compound 22)

To a solution of 0.080 g (0.18 mmol) of ethyl 4-(2-(4,4-dimethyl-3,4-dihydro-N-(4-methylphenyl)-2(1H)-quinolinon-7-yl)ethynyl)benzoate (Compound 21) in 4.0 mL of tetrahydrofuran and 1.0 mL of methanol was added 1.0 mL (1.3 mmol) of 1.3M aqueous LiOH. The resulting solution was heated at 50° C. for 5 hours. The mixture was concentrated in vacuo, water was added, and the mixture was extracted with ether (2x). The combined organic layers were washed with brine, dried (MgSO$_4$), filtered, and concentrated in vacuo. The resulting crude product was purified by recrystallization from acetonitrile to give the title compound as a yellow solid. PNMR (500 MHz, DMSO) d 1.31 (6 H, s), 2.35 (3 H, s), 2.59 (2 H, s), 6.32 (1 H, d, J=7.1 Hz), 7.10 (1 H, d, J=8.3 Hz), 7.23 (1 H, dd, J=8.1, 1.7 Hz), 7.32 (1 H, d, J=8.3 Hz), 7.42 (1 H, d, J=8.1 Hz), 7.51 (1 H, d, J=8.3 Hz), 7.84 (1 H, d, J=8.3 Hz).

4,4-Dimethyl-1,2,3,4-tetrahydro-N-(4-methylphenyl)-7-carboxyquinoline (Compound 23).

To a solution of 0.26 g (0.79 mmol). 4,4-dimethyl-1,2,3,4-tetrahydro-N-(4-methylphenyl)-7-bromoquinoline (Compound 1) in 6.0 mL of tetrahydrofuran stirring at −78° C. under argon was added 0.90 mL (1.4 mmol, 1.6M in hexanes) of n-butyllithium and the reaction was stirred at −78° C. for 25 minutes. Carbon dioxide was then bubbled into the reaction mixture while it was stirred at −78° C. to room temperature for 18 hours. Thereafter 10% HCl was added and the mixture was extracted with ethyl acetate (2x). The combined organic layers were then washed with brine, dried (Na$_2$SO$_4$), filtered and concentrated in vacuo to give the title compound as an orange solid. PNMR (300 MHz, d6 acetone) d 1.37 (6 H, s), 1.88 (2 H, t, J=6.0 Hz), 2.33 (3 H, s), 3.63 (2 H, t, J=6.0 Hz), 7.16 (2 H, d, J=8.4 Hz), 7.24 (2 H, d, J=8.4 Hz), 7.26 (1 H, d, J=1.7 Hz), 7.32 (1 H, rid, J=8.0, 1.7 Hz), 7.37 (1 H, d, J=8.0 Hz).

(4,4-dimethyl-1,2,3,4-tetrahydro-N-(4-methylphenyl) quinolin-7-carboxyl)-4-carboethoxyanilide (Compound 24).

To a solution of 0.12 g (0.41 mmol) of 4,4-dimethyl-1,2,3,4-tetrahydro-N-(4-methylphenyl)-7-carboxyquinoline (Compound 23) in 1.0 mL of methylene chloride was added 1.4 g (1.0 mL, 11.5 mmol) of oxalyl chloride and the reaction mixture was heated for 40 min at which time escape of gas by bubbling from the reaction mixture had ceased. The mixture was cooled and the excess oxalyl chloride was removed in vacuo. The residue was dissolved in 6.0 mL of methylene chloride. To this were added 86 mg (0.52 mmol) of ethyl 4-aminobenzoate and 1.0 mL of triethylamine and the reaction mixture was stirred at room temperature for 1.5 hours. Water was added, and the mixture was extracted with ethyl acetate (2x). The combined organic layers were washed with brine, dried (Na$_2$SO$_4$), filtered, and concentrated in vacuo. The mixture was purified by flash chromatography (10% ethyl acetate in hexanes) to give the title compound as a dark solid. PNMR (300 MHz, CDCl$_3$) d 1.39 (6 H, s), 1.40 (3 H, t, J=7.1 Hz), 1.88 (2 H, t, J=6.0 Hz), 2.35 (3 H, s), 3.60 (2 H, t, J=6.0 Hz), 4.36 (2 H, q, J=7.1 Hz), 7.11–7.16 (4 H, m), 7.21 (2 H, d, J=8.5), 7.35 (1 H, d, J=8.5 Hz), 7.63 (2 H, d, J=8.7 Hz), 7.78 (1 H, s, NH), 8.01 (2 H, d, J=8.7 Hz).

(4,4-dimethyl-1,2,3,4-tetrahydro-N-(4-methylphenyl) quinolin-7-carboxyl)-4-carboxyanilide (Compound 25)

To a solution of 16 mg (0.04 mmol) of (4,4-dimethyl-1,2,3,4-tetrahydro-N-(4-methylphenyl)-7-quinolinyl)-4-carboethoxyanilide (Compound 24) in 1.0 mL of tetrahydrofuran and 0.5 mL of methanol was added 0.5 mL (0.2 mmol) of 0.4M aqueous LiOH. The resulting solution was heated at 50° C. for 3 hours. The mixture was concentrated in vacuo, water was added, and the mixture was extracted with ether (2x). The combined organic layers were washed with brine, dried (MgSO$_4$), filtered, and concentrated in vacuo to give the title compound as a yellow solid. NMR (300 MHz, d6 acetone) d 1.38 (6 H, s), 1.89 (2 H, t, J=6.0 Hz), 2.33 (3 H, s), 3.60 (2 H, t, J=6.0 Hz), 7.17 (2 H, t, J=8.6 Hz), 7.20–7.22 (3 H, m), 7.25 (1 H, dd, J=8.1, 1.8 Hz), 7.38 (1 H, d, J=8.1 Hz), 7.89 (2 H, d, J=8.8 m), 7.98 (2 H, d, J=8.8 Hz), 9.52 (1 H, s, NH).

What is claimed is:

1. A compound of the formula

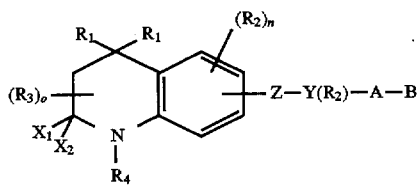

where $R_1$ is independently H or alkyl of 1 to 6 carbons;

$R_2$ is lower alkyl of 1 to 6 carbons, F, Cl, Br, or I;

n is an integer between the values 0 and 3;

$R_3$ is lower alkyl of 1 to 6 carbons or F;

o is an integer between the values 0–2;

$X_1$ and $X_2$ independently are H, or alkyl of 1 to 6 carbons, or the $X_1$ and $X_2$ groups jointly symbolize an oxo (=O) function;

$R_4$ is phenyl, naphthyl or, thienyl, said phenyl, naphthyl and thienyl groups being optionally substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, or $COOR_1$;

Z is —C≡C—,

—$(CR_1=CR_1)_{n'}$— where n' is an integer having the value 0–5,

—CO—$NR_1$—, or

—$NR_1$—CO,

Y is a phenyl or naphthyl group, or heteroaryl selected from a group consisting of pyridyl, and thienyl, said phenyl and heteroaryl groups being optionally substituted with one or two $R_2$ groups, or when Z is —$(CR_1=CR_1)_{n'}$— and n' is 3, 4 or 5 then Y represents a direct valence bond between said $(CR_2=CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cydoalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound of claim 1 where Y is phenyl, naphthyl, pyridyl, or thienyl.

3. A compound of claim 2 where Y is phenyl and the phenyl group is substituted in the 1 and 4 (para) positions by the Z and A—B groups.

4. A compound of claim 1, where the A—B group is $(CH_2)_q$COOH or $(CH_2)_q$—$COOR_8$.

5. A compound of claim 1 where the —Z—Y($R_2$)—A—B group is attached to the tetrahydroquinoline moiety in the 6 or 7 position of the tetrahydroquinoline moiety.

6. A compound of claim 5 where the —Z—Y($R_2$)—A—B group is attached to the tetrahydroquinoline moiety in the 7 position of the trahydroquinoline moiety.

7. A compound of claim 1 where $X_1$ and $X_2$ both are H or lower alkyl.

8. A compound of claim 1 where $X_1$ and $X_2$ jointly represent an oxo (=O) group.

9. A compound of claim 1 where the Z group is selected from the group consisting of —C≡C—, —CH=CH—, —CONH—, —NHCO—, or —$(CR_1=CR_1)_{n'}$— where n' is 5, and —$(CR_1=CR_1)_{n'}$— where n' is 0.

10. A compound of claim 9 where $R_4$ is phenyl, alkyl or halogen substituted phenyl, thienyl, and alkyl or halogen substituted thienyl.

11. A compound of the formula

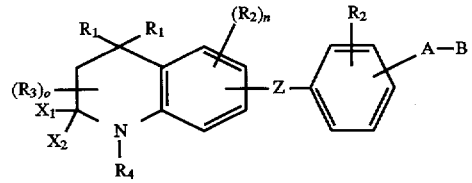

where $R_1$ is independently H or alkyl of 1 to 6 carbons;

$R_2$ is hydrogen, lower alkyl of 1 to 6 carbons or fluorine;

n is an integer between the values 0 and 3;

$R_3$ is lower alkyl of 1 to 6 carbons;

o is an integer between the values 0–2;

$X_1$ and $X_2$ independently are H, or alkyl of 1 to 6 carbons, or the $X_1$ and $X_2$ groups jointly symbolize an oxo (=O) function;

$R_4$ is phenyl or naphthyl, said phenyl or naphthyl groups being optionally substituted with one to three $R_5$ groups, where $R_5$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, COOH, or $COOR_1$;

Z is —C≡C—, —$CR_1$=$CR_1$—, or —CO—NH— and the Z group is attached to the 6 or 7 position of the tetrahydroquinoline moiety;

A is $(CH_2)_q$ where q is 0–5, and

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

12. A compound of claim 11 where both $X_1$ and $X_2$ groups are hydrogen.

13. A compound of claim 11 where the $X_1$ and $X_2$ groups jointly represent an oxo (=O) group.

14. A compound of claim 11 where Z is —C≡C—.

15. A compound of claim 11 where Z is —CR$_1$=CR$_1$—
16. A compound of claim 11 where Z is —CO—NH—.
17. A compound of claim 11 where R$_4$ is phenyl or (4-methyl)phenyl.
18. A compound of claim 11 where q is 0, and B represents COOR$_8$, CONR$_9$R$_{10}$ COOH or a pharmaceutically acceptable salt thereof.
19. A compound of claim 11 where the phenyl group is substituted in the 1,4 positions by the Z and A—B groups.
20. A compound of the formula

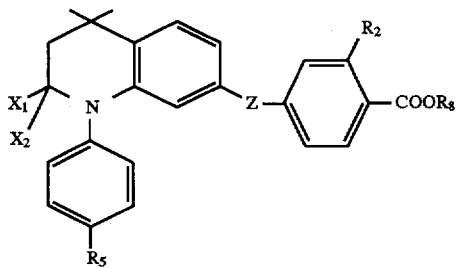

where X$_1$ and X$_2$ independently are H or the X$_1$ and X$_2$ groups jointly symbolize an oxo (=O) function;
R$_1$ is independently H or alkyl of 1 to 6 carbons;
R$_2$ is hydrogen or fluorine.
R$_5$ is H or methyl;
Z is —C≡C—, —CR$_1$=CR$_1$— or —CO—NH—;
R$_8$ is H, methyl or ethyl.

21. A compound of claim 20 where both X$_1$ and X$_2$ are hydrogen.
22. A compound of claim 21 where Z is —C≡C—.
23. A compound of claim 22 where R$_5$ is hydrogen.
24. A compound of claim 23 where R$_2$ is hydrogen.
25. A compound of claim 24 where R$_8$ is hydrogen or ethyl.
26. A compound of claim 22 where R$_5$ is methyl.
27. A compound of claim 26 where R$_2$ is hydrogen.
28. A compound of claim 27 where R$_8$ is hydrogen or ethyl.
29. A compound of claim 26 where R$_2$ is fluoro.
30. A compound of claim 29 where R$_8$ is hydrogen or ethyl.
31. A compound of claim 20 where the X$_1$ and X$_2$ groups jointly represent an oxo (=O) group, Z is —C≡C—, R$_5$ is methyl, and R$_2$ is hydrogen.
32. A compound of claim 31 where R$_8$ is hydrogen or ethyl.
33. A compound of claim 21 where Z is —CH=CH—, R$_5$ is methyl, and R$_2$ is hydrogen.
34. A compound of claim 33 where R$_8$ is hydrogen or ethyl.
35. A compound of claim 21 where Z is —CO—NH—, R$_5$ is methyl, and R$_2$ is hydrogen.
36. A compound of claim 35 where R$_8$ is hydrogen or ethyl.

* * * * *

UNITED STATES PATENT AND TRADEMARK OFFICE
CERTIFICATE OF CORRECTION

PATENT NO.   : 5,739,338
DATED        : April 14, 1998
INVENTOR(S)  : Beard et al.

It is certified that error appears in the above-identified patent and that said Letters Patent is hereby corrected as shown below:

Column 1,
Please insert the following under 'FOREIGN PATENT DOCUMENTS".
-- 0303186    2/1989  European Pat. Off. --.
-- 0412387    2/1991  European Pat. Off. --.
-- 0617020    9/1994  European Pat. Off. --.
-- 0661258    7/1995  European Pat. Off. --.

Column 2,
Line 12, "deserve" should be -- describe --.
Line 38, "RXBp" should be -- $RXR_\beta$ --.

Column 3,
Line 27, "Augusty" should be -- August --.

Column 5,
Line 24, "Or" should be -- or --.

Column 6,
Line 16, "descried" should be -- described --.

Column 7,
Line 17, "RARβ" should be -- $RAR_\beta$ --.
Line 65, "ache" should be -- acne --.

Column 8,
Line 39, "ache" should be -- acne --.
Line 27, "effects" should be -- affects --.

Column 9,
line 6, "admistered" should be -- adminstered --.
Line 45, "effects" should be -- affects --.

Column 10,
Line 8, "branch chain" should be -- branched-chain --.
Lines 10-11, "branch chain" should be -- branched-chain --.

Column 11,
Line 40, after "to", delete "a".
Line 64, after "with", delete "an".

UNITED STATES PATENT AND TRADEMARK OFFICE
CERTIFICATE OF CORRECTION

PATENT NO.    : 5,739,338
DATED         : April 14, 1998
INVENTOR(S)   : Beard et al.

It is certified that error appears in the above-identified patent and that said Letters Patent is hereby corrected as shown below:

Column 12,
Lines 22-23, "dicyclohexylcarbodfimide" should be -- dicyclohexylcarbodiimide --.

Column 13,
Line 16, after "C", delete ".".
Line 19, "Alcohols ..." should begin a new paragraph.
Line 37, "Oreurn" should be -- Omura --.
Line 46, after "from", delete ".".
Lines 54-5, "substititutions" should be -- substitutions --.
Line 66, "CH$_2$)$_1$-(COOR$_8$" should be -- (CH$_2$)$_q$-COOR$_8$ --.

Column 14,
Line 22, -(CR$_1$=CR$_1$)n,-" should be -- -(CR$_1$=CR$_1$)$_n$,- --.

Column 18,
Line 61, "(R2)" should be -- (R$_2$) --.

Column 22,
Line 10, "-(CR$_1$=CR$_1$,-" should be -- -CR$_1$=CR$_1$)$_n$,- --.

Column 23,
Line 48, after "3,6", delete ",".

Column 25,
Line 61, "subtituents" should be -- substituents --.

Column 27,
Line 31, "Nail" should be -- NaH --.
Line 46, "round-buttom" should be -- round-bottom --.

Column 28,
Line 8, "4,4-Dimethyl- ..." should begin a new line.
Line 21, "dear" should be -- clear --.
Line 41, "rid" should be -- dd --.
Line 55, "(MgSO4)" should be -- (MgSO$_4$) --.

UNITED STATES PATENT AND TRADEMARK OFFICE
CERTIFICATE OF CORRECTION

PATENT NO. : 5,739,338
DATED : April 14, 1998
INVENTOR(S) : Beard et al.

It is certified that error appears in the above-identified patent and that said Letters Patent is hereby corrected as shown below:

Column 29,
Line 59, "palladium ($I_D$" should be -- palladium(II) --.

Column 30,
Line 14, "rid" should be -- dd --.

Column 32,
Line 46, "rid" should be -- dd --.

Column 34,
Line 23, "rid" should be -- dd --.
Line 65, "8.8m" should be -- 8.8Hz --.

Column 35,
Line 50, "cydoalkyl" should be -- cycloalkyl --.

Column 36,
Line 6, "trahydroquinolime" should be -- tetrahydro-quinoline --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*